United States Patent
Koide et al.

(10) Patent No.: US 8,526,998 B2
(45) Date of Patent: Sep. 3, 2013

(54) MOBILE TERMINAL HAVING PULSE METER

(75) Inventors: Tomoko Koide, Osaka (JP); Satoyuki Sasaki, Osaka (JP); Takemi Katoh, Osaka (JP); Satoshi Kyohgoku, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 297 days.

(21) Appl. No.: 12/992,612

(22) PCT Filed: Apr. 10, 2009

(86) PCT No.: PCT/JP2009/057329
§ 371 (c)(1),
(2), (4) Date: Nov. 15, 2010

(87) PCT Pub. No.: WO2009/139244
PCT Pub. Date: Nov. 19, 2009

(65) Prior Publication Data
US 2011/0065482 A1  Mar. 17, 2011

(30) Foreign Application Priority Data

May 16, 2008 (JP) ................................. 2008-130037
Dec. 11, 2008 (JP) ................................. 2008-315749

(51) Int. Cl.
*H04M 1/00* (2006.01)
(52) U.S. Cl.
USPC ..................................... 455/550.1; 455/575.1
(58) Field of Classification Search
USPC ............. 455/550.1, 566, 575.1, 575.3, 575.4, 455/575.6, 90.3, 557
See application file for complete search history.

(56) References Cited

U.S. PATENT DOCUMENTS

| | | | |
|---|---|---|---|
| 6,526,315 B1 | 2/2003 | Inagawa et al. | |
| 7,283,850 B2 * | 10/2007 | Granovetter et al. | 455/570 |
| 7,764,641 B2 * | 7/2010 | Pelton et al. | 370/328 |
| 2006/0172764 A1 | 8/2006 | Makino | |
| 2009/0054067 A1 * | 2/2009 | Gauthier et al. | 455/440 |

FOREIGN PATENT DOCUMENTS

| | | |
|---|---|---|
| CN | 2687981 Y | 3/2005 |
| DE | 102 19 675 A1 | 11/2003 |
| JP | 8-66378 A | 3/1996 |
| JP | 2001-276012 A | 10/2001 |
| JP | 2003-298711 A | 10/2003 |
| JP | 2006-054727 * | 2/2006 |
| JP | 2006-54727 A | 2/2006 |

(Continued)

OTHER PUBLICATIONS

European Search report for corresponding European patent application No. 09746451.5, dated May 14, 2012.

*Primary Examiner* — Ping Hsieh
(74) *Attorney, Agent, or Firm* — Birch, Stewart, Kolasch & Birch, LLP

(57) ABSTRACT

A mobile terminal (10) of the present invention has a sensor (15) for detecting a pulse, in an upper end portion of a back surface of a main body of the mobile terminal (10). The sensor (15) is constituted by a light-emitting element and a light-receiving element. A position of the sensor is determined so that a force acting on the sensor falls within a range from 50 gf to 200 gf in a case where the mobile terminal is supported at its lower end portion and at the sensor by a fingertip. Thus, the present invention provides the mobile terminal (10) which can be always carried with a user and which realizes easy and stable pulse measurement.

12 Claims, 21 Drawing Sheets

(56) References Cited

FOREIGN PATENT DOCUMENTS

| JP | 2006-211576 A | 8/2006 |
| JP | 2006-51279 A | 10/2006 |
| JP | 2006-287481 A | 10/2006 |
| JP | 2007-207172 A | 8/2007 |
| JP | 2007-274373 A | 10/2007 |
| JP | 2007-295115 A | 11/2007 |
| JP | 3136727 U | 11/2007 |
| JP | 2008-85777 A | 4/2008 |

* cited by examiner (a)

(b)

(a)

(b)

(a)

(b)

(a)

(b)

(c)

(d)

MOBILE TERMINAL HAVING PULSE METER

TECHNICAL FIELD

The present invention relates to mobile terminals typified by mobile phones, particularly to mobile terminals having a pulse meter.

BACKGROUND ART

Recently, people, especially the middle-aged and senior, are becoming health-conscious, as typically seen in frequent appearances of the word "metabolic syndrome" on newspapers, and accordingly, actively take exercises such as jogging and exercises using a training device such as a bicycle ergometer. It is said that one needs to pay sufficient attention to his physical condition when taking such an exercise. For example, it is said to be good to monitor an exercise load by checking pulse etc. so as to prevent excessive exercise.

Against this backdrop, a pulse meter which makes it possible to easily take one's own pulse anywhere and anytime is sought after, and accordingly, portable pulse meters have been proposed. There are various types of pulse meters. Recently-proposed one is a pulse meter in which a pulse sensor is realized by a photointerrupter which emits and receives infrared rays or the like. Such a pulse meter is used as a small portable pulse meter.

Patent literature 1 discloses a bioelectric impedance measurement device which has a photointerrupter so as to additionally measure a pulse rate.

FIG. 24 is a schematic view illustrating the bioelectric impedance measurement device. In FIG. 24, 245 indicates a main body 245 of the bioelectric impedance measurement device. A surface of the main body 245 is provided with (i) a display section 246, (ii) an electrode group 247 which is made up of a plurality of electrodes, and (iii) a sensor 248 which is known as a reflective photointerrupter and into which a light-emitting element and a light-receiving element are incorporated.

The bioelectric impedance measurement device allows a user to know his body fat by touching the electrode group 247 with his fingertip or the like so that his bioimpedance is measured. Further, the sensor 248 of the bioelectric impedance measurement device makes it possible to measure a pulse rate. The following shows only a simple overview of how to measure a pulse rate by using a photointerrupter. Since it is already known how the pulse rate is measured by a photointerrupter, details thereof are omitted in the following.

First, a test subject touches the sensor 248 with his fingertip. Then, the light-emitting element generates infrared rays so as to irradiate a blood vessel of the fingertip with the infrared rays. Then, the light-receiving element receives light reflected from the blood vessel so as to detect a change in blood flow volume inside the blood vessel which change is caused in accordance with a heartbeat. A pulse rate is calculated on the basis of the detected results. In actual measurement, the test subject keeps touching the sensor 248 with his fingertip for a certain time.

Patent Literature 2 discloses an optical pulse sensor which is provided to an exercise machine such as a bicycle ergometer. FIG. 25 is a view illustrating the pulse sensor which is worn by pinching an earlobe. In FIG. 25, 250 indicates pinching members for pinching an earlobe therebetween. A sensor 251 is provided to tip sections of the pinching members. The sensor 251 is realized by a photointerrupter made up of a light-emitting element and a light-receiving element. In this example, a transmissive photointerrupter is adopted as the sensor 251. However, the pulse sensor operates, as a pulse meter, on the same operating principle as the art disclosed in Patent Literature 1. The sensor 251 is connected with a cord 252. An output of the sensor 251 is supplied to a main body (not illustrated) via the cord 252. The main body calculates a pulse rate on the basis of the output from the sensor 251 so as to display the calculation result on a display apparatus (not illustrated).

CITATION LIST

Patent Literature 1

Japanese Patent Application Publication, Tokukai, No. 2001-276012 A (Publication Date: Oct. 9, 2001)

Patent Literature 2

Japanese Patent Application Publication, Tokukaihei, No. 8-66378 A (Publication Date: Mar. 12, 1996)

SUMMARY OF INVENTION

The pulse meter disclosed in Patent Literature 1 is small and easy to carry with a user. This allows a user to measure pulse whenever necessary. Therefore, a user can carry such a pulse meter with himself so as to monitor his physical condition. This makes it possible for him to control an exercise intensity so that the exercise intensity may not be an excessive load.

However, the pulse meter disclosed in Patent Literature 1 has a problem in that in actual use, a user cannot easily perform stable pulse measurement, and he is required to be considerably proficient to the pulse meter. Furthermore, the pulse meter, which is so small and easy to carry with a user, has another problem such that a user forgets to carry the pulse meter with himself when leaving for exercise, so as to find out that he does not have the pulse meter when he would like to measure pulse.

The pulse meter disclosed in the Patent Literature 2 is a pulse meter of a type to be used by pinching an earlobe. Therefore, a relatively stable measurement can be realized. However, the pulse meter is not intended to be carried with a user, as seen from, for example, the fact that the pulse meter separately has a sensor and a main body which calculates a pulse rate on the basis of an output from the sensor. Further, since the pulse meter is used by pinching an earlobe, some users feel discomfort in use of the pulse meter. Further, the sensor is considerably large. Thus, the pulse sensor is not suitable for mobile terminals or the like which are required to be small as possible.

The inventors of the present invention conducted various analyses to find the reason why a pulse meter such as the one disclosed in Patent Literature 1 requires considerable proficiency to the pulse meter. As a result, the inventors found that for a stable pulse measurement, it is necessary that a force within a specific range be applied between a fingertip and the sensor realized by, e.g., a photointerrupter, and the force is stable within the specific range.

Mobile terminals such as mobile phones are used very widely as typical devices which are always carried with users. Accordingly, most people carry such mobile terminals with themselves whenever going out. The inventors of the present invention found that weights of the mobile terminals can suitably serve as a load for stable pulse measurement, by contriving where to provide the sensor and how to hold the mobile terminal.

The present invention was made in view of the problems of the conventional arts and in view of the knowledge of the inventors of the present invention. An object of the present invention is to provide a pulse meter being combined with a mobile terminal which is likely to be always carried with a user, and being capable of stably measuring a pulse rate.

In order to attain the object, a mobile terminal of the present invention includes: a main body housing an electronic device; a display section or an operation section, being provided on a first surface of the main body; and a sensor for detecting a pulse, the sensor being provided to a first end portion of a second surface of the main body, the sensor including a light-emitting element and a light-receiving element, and the sensor being provided so that a force acting on the sensor falls within a range from 50 gf to 200 gf in a case where the mobile terminal is supported from below at a position of the sensor and at a position in a second end portion of the second surface.

The invention makes it possible to support the mobile terminal at two or three points so that a fingertip may be put on the sensor while a palm supports the second end portion. This makes it possible to apply, to the fingertip, a weight required for stable pulse measurement, with stably supporting the mobile terminal. As a result, the fingertip and the sensor stably have contact with each other. This makes it possible to measure a pulse rate easily and accurately in a short time. In addition, according to the arrangement, a pulse meter is combined with a mobile terminal which is likely to be always carried with a user. This prevents a user from forgetting the pulse meter when, e.g., going out, and allows a user to know his pulse rate anywhere and whenever necessary.

In order to attain the object, a mobile terminal of another invention of the present application includes: a main body housing an electronic device; and a sensor for detecting a pulse, the main body being constituted by a first casing having a display section on its first surface, a second casing having an operation section on its first surface, and a joint for foldably joining the first casing and the second casing so that the first surface of the first casing and the first surface of the second casing may face each other, the sensor being provided to a first end portion of a second surface of the second casing, the first end portion being closer to the joint than a second end portion of the second casing, and the sensor being provided so that a force acting on the sensor falls within a range from 50 gf to 200 gf in a case where the mobile terminal is supported from below at a position of the sensor and at a position in the second end portion of the second surface of the second casing.

In addition to the effect above, the invention makes it possible to use a pulse meter of a relatively heavy foldable mobile terminal in a folded state. This improves the pulse meter in terms of convenience.

In order to attain the object, a mobile terminal of further another invention of the present application further includes: a three-dimensional acceleration sensor; a pulse sensor axis storing section; and a pulse sensor direction determining section, on the basis of (i) information indicative of an attitude of the mobile terminal which attitude is detected by the three-dimensional acceleration sensor and (ii) pulse sensor axis information supplied from the pulse sensor axis storing section, the mobile terminal determining, in pulse measurement, whether or not the sensor is directed in the gravitational direction, in order to notify a user of whether or not the mobile terminal is in a proper attitude.

This makes it possible to avoid pulse measurement in which the mobile terminal is in a wrong attitude. As a result, it becomes possible to reduce the risk that incorrect information is presented to a user with regard to his pulse rate.

For a fuller understanding of the nature and advantages of the invention, reference should be made to the ensuing detailed description taken in conjunction with the accompanying drawings.

Figure 1:
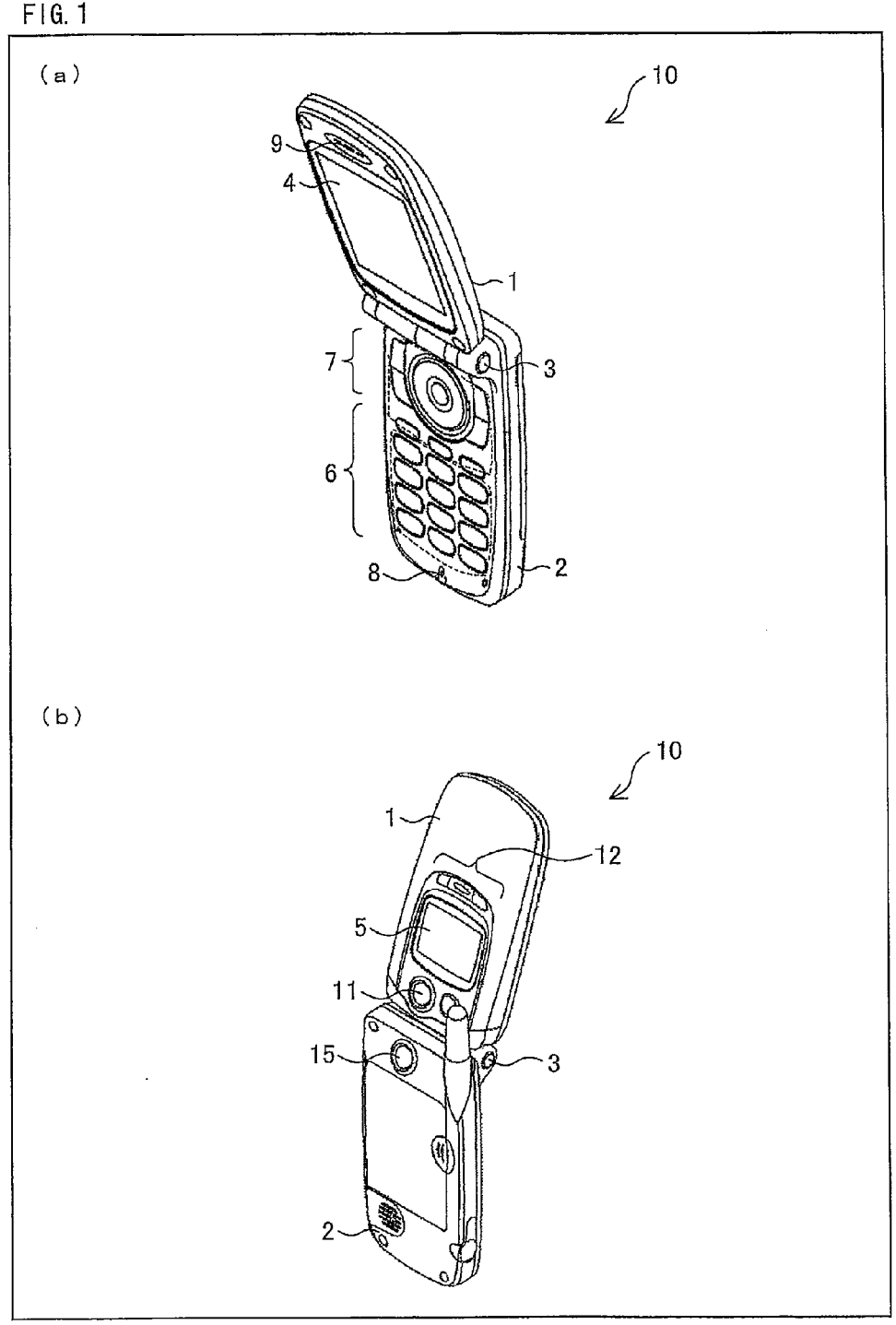
FIG. 1

Each of (a) and (b) of FIG. 1 is a view illustrating an arrangement of that mobile phone of a first embodiment of the present invention which has a pulse meter.

FIG. 2

Figure 2:
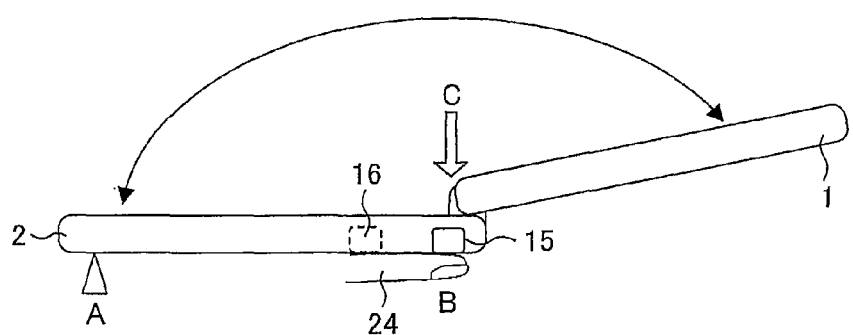
Figure 2:
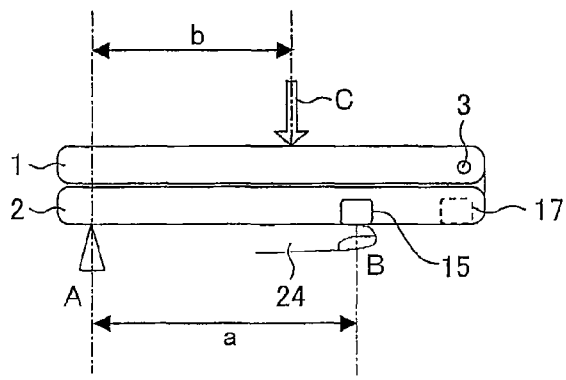

Each of (a) and (b) of FIG. 2 is a view illustrating a method for easily and stably measuring a pulse rate by using the mobile phone of the first embodiment.

FIG. 3

Figure 3:
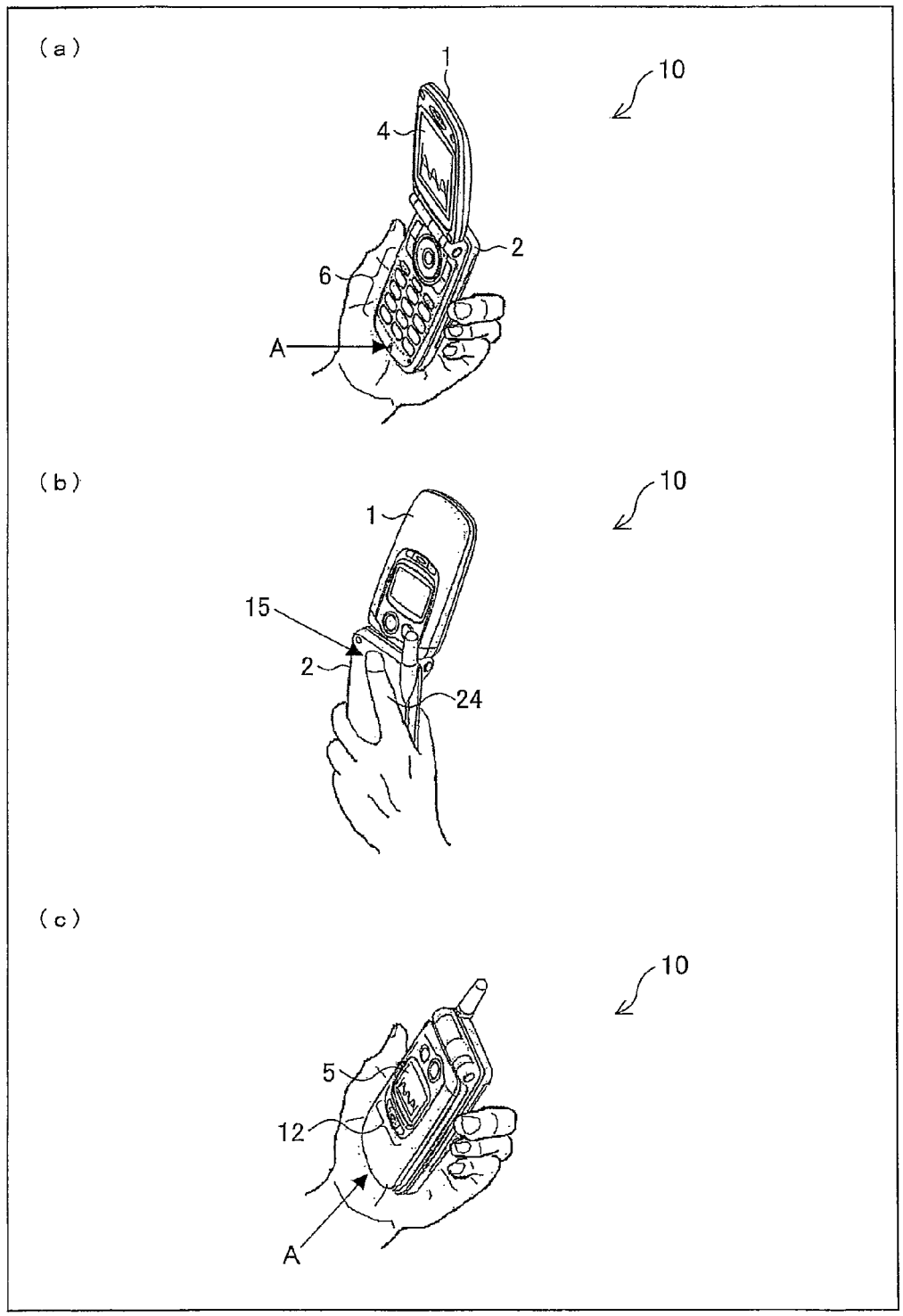

(a), (b), and (c) of FIG. 3 are views illustrating how the mobile phone of the first embodiment is supported in pulse measurement.

FIG. 4

Figure 4:
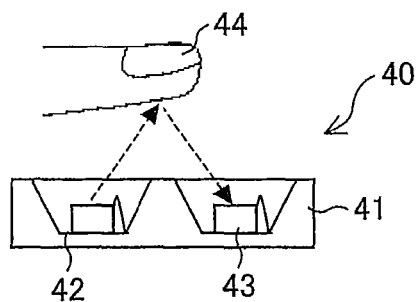

FIG. 4 is a view illustrating an arrangement of a reflective photointerrupter which is provided in a sensor of a pulse meter.

FIG. 5

Figure 5:
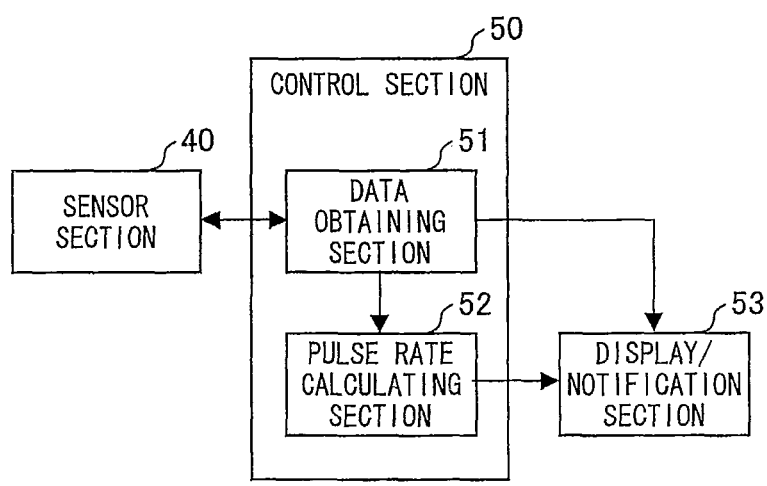

FIG. 5 is a block diagram showing an arrangement of a pulse meter.

FIG. 6

Figure 6:
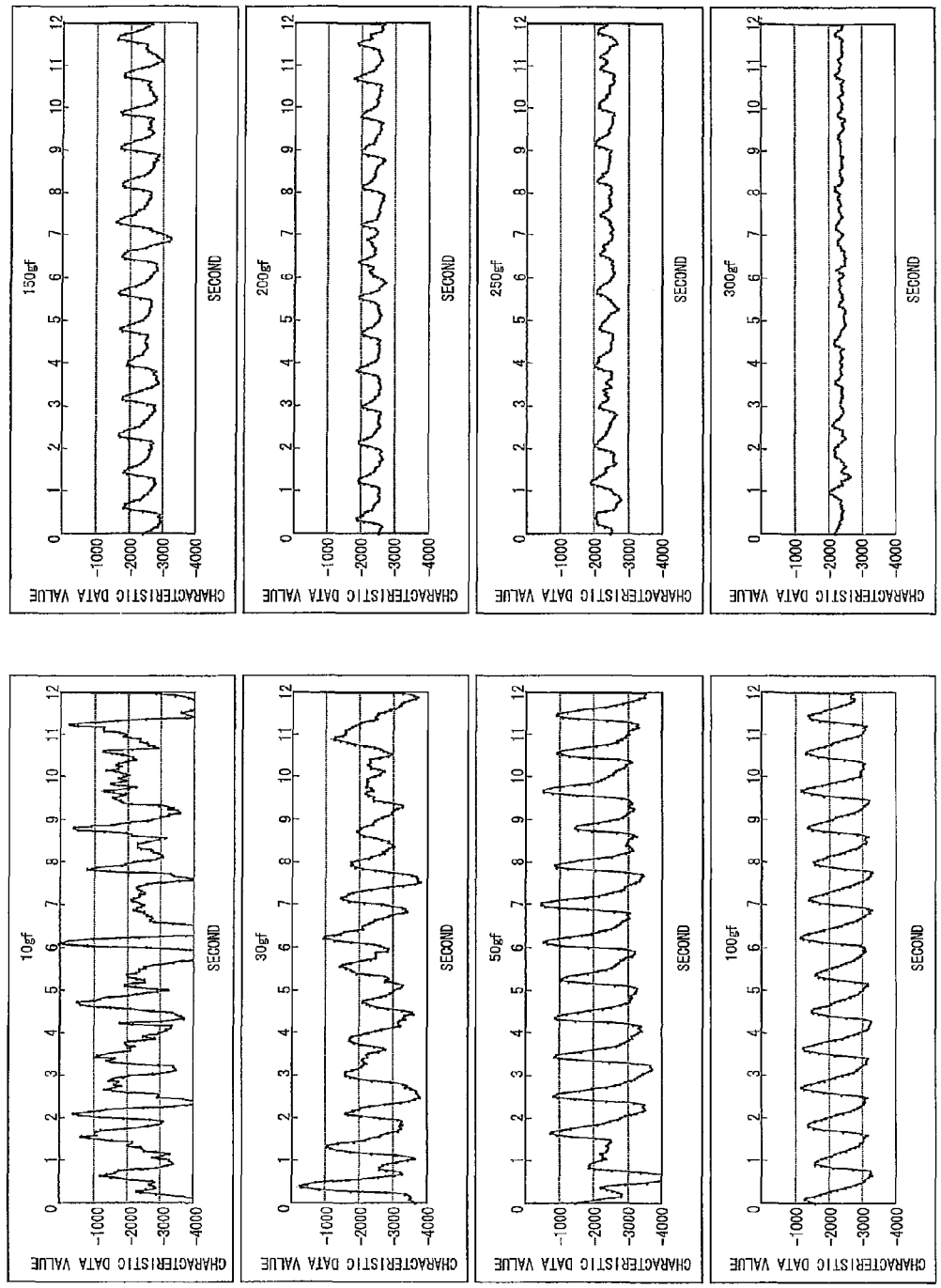

FIG. 6 is graphs each showing a force acting on the sensor of the pulse meter and a sensor output.

FIG. 7

Figure 7:
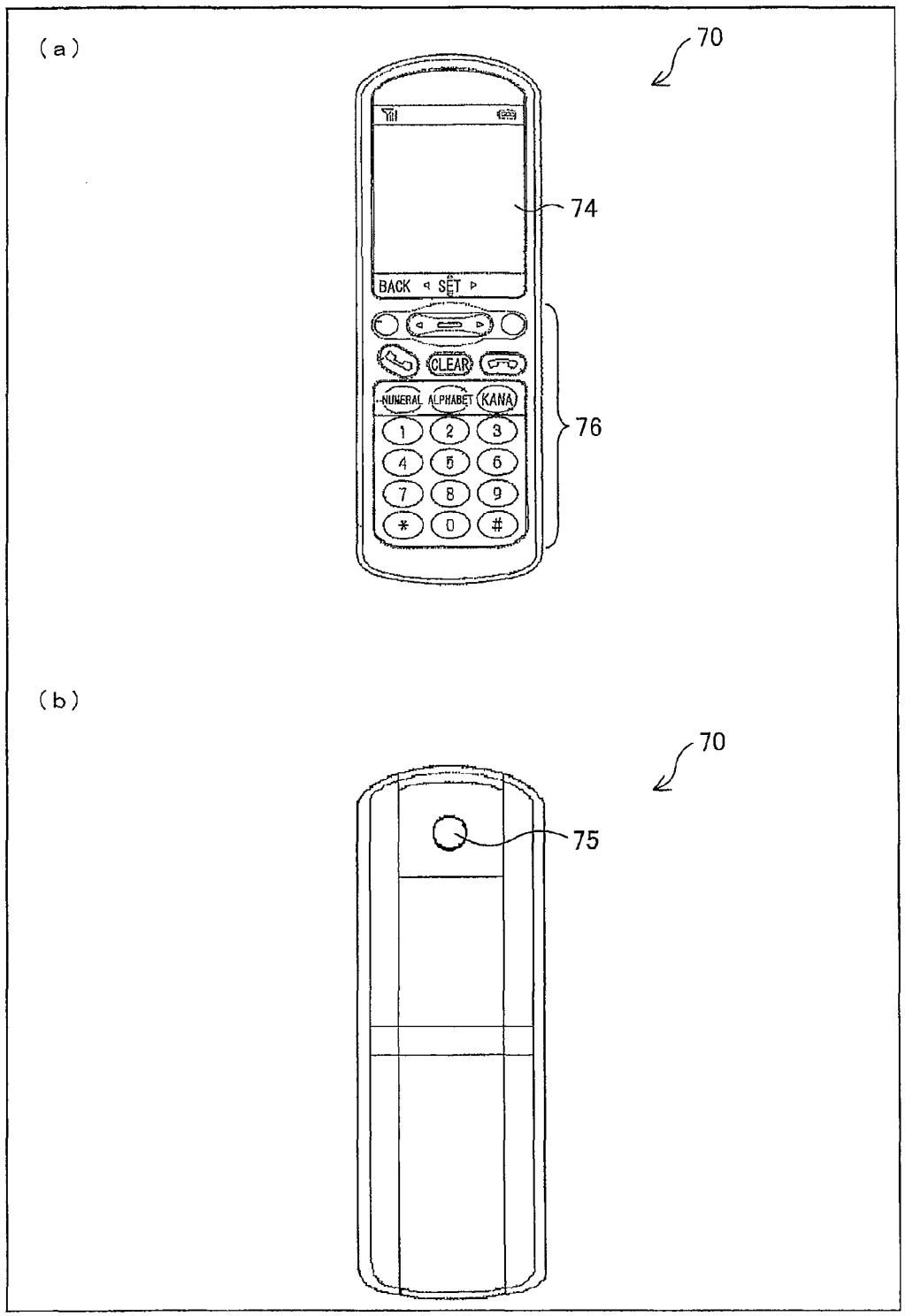

Each of (a) and (b) of FIG. 7 is a view illustrating an arrangement of that mobile phone of a second embodiment of the present invention which has a pulse meter.

FIG. 8

Figure 8:
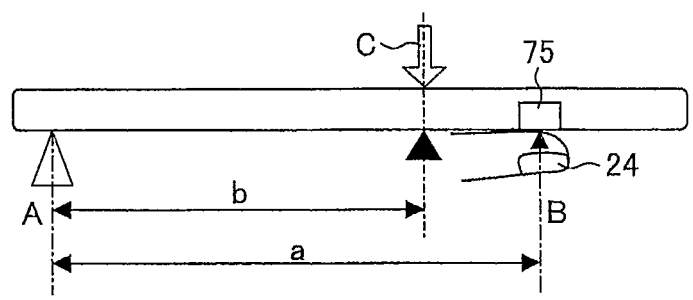

FIG. 8 is a view illustrating a method for easily and stably measuring a pulse rate by using the mobile phone of the second embodiment.

FIG. 9

Figure 9:
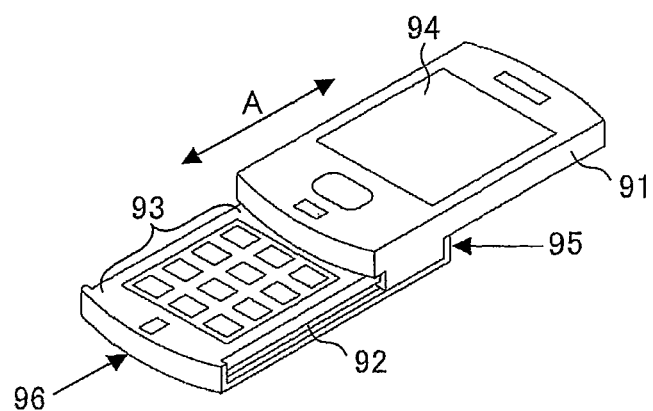

FIG. 9 is a view illustrating an arrangement of that mobile phone of a third embodiment of the present invention which has a pulse meter.

FIG. 10

Figure 10:
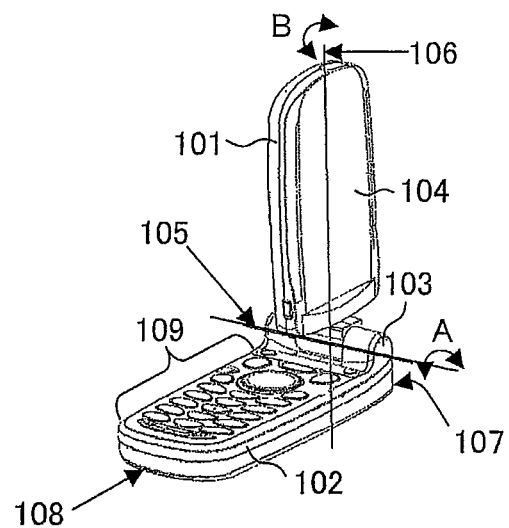

FIG. 10 is a view illustrating an arrangement of that mobile phone of a fourth embodiment of the present invention which has a pulse meter.

FIG. 11

Figure 11:
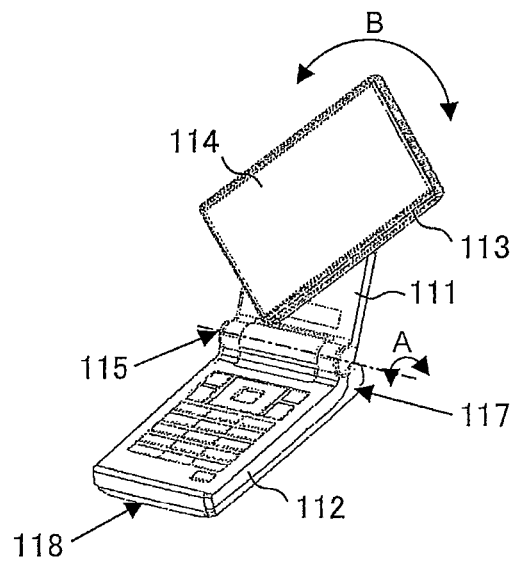

FIG. 11 is a view illustrating an arrangement of that mobile phone of a fifth embodiment of the present invention which has a pulse meter.

FIG. 12

Figure 12:
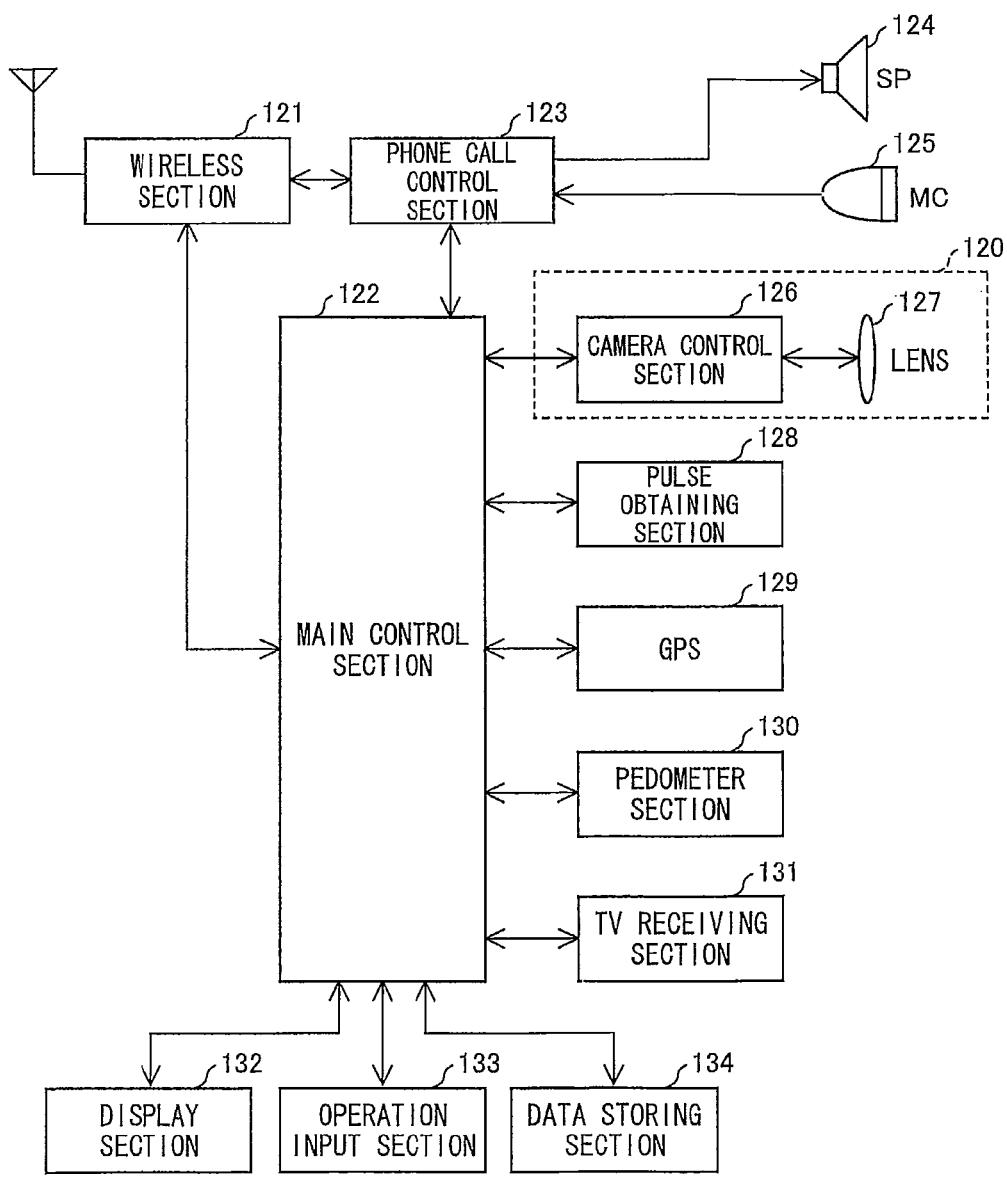

FIG. 12 is a block diagram showing an arrangement of that mobile phone of a sixth embodiment of the present invention which has a pulse meter.

FIG. 13

Figure 13:
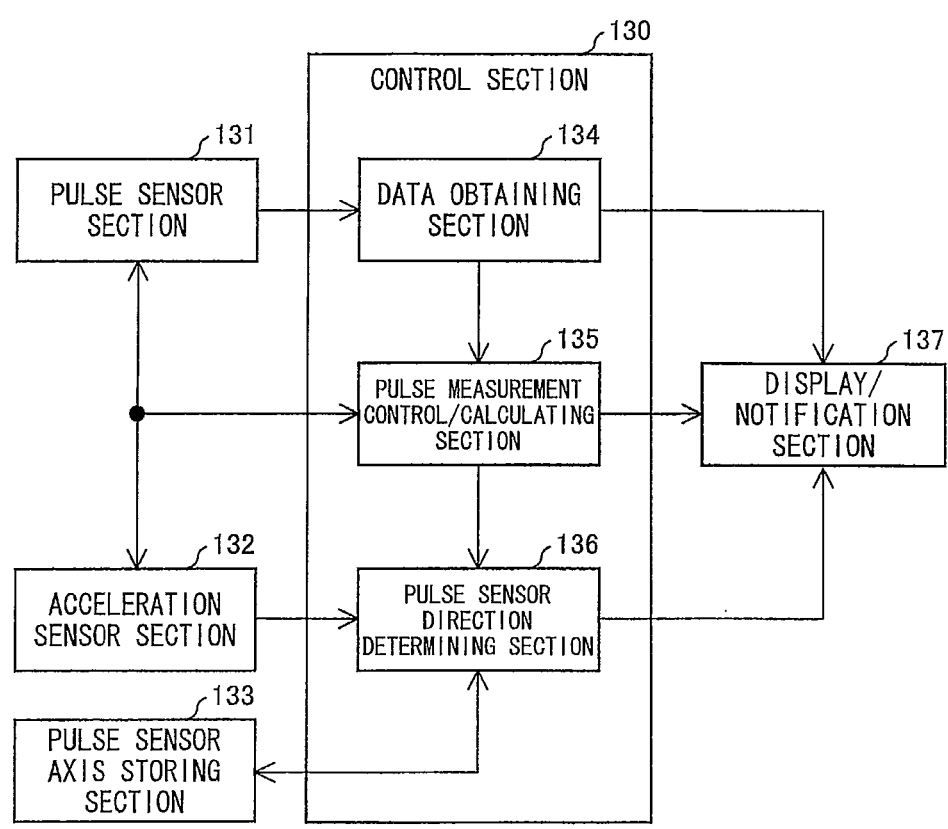

FIG. 13 is a block diagram showing a main part of an arrangement of that mobile device of a seventh embodiment of the present invention which has a pulse meter.

FIG. 14

Figure 14:
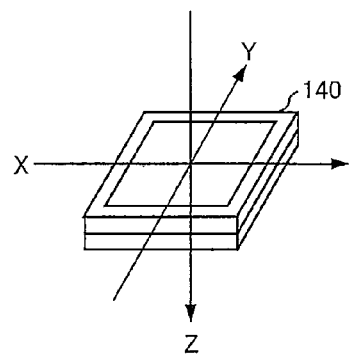
Figure 14:
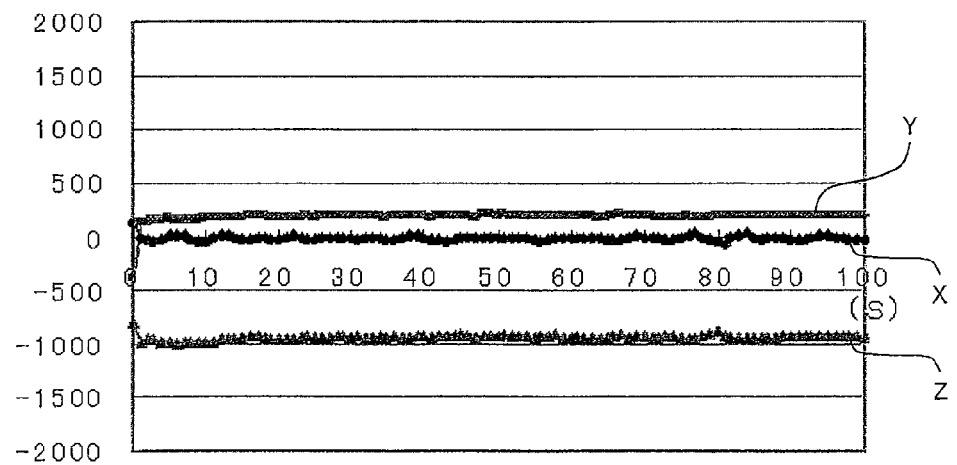

(a) and (b) of FIG. 14 are a view and a graph showing how a three-dimensional acceleration sensor operates.

FIG. 15

Figure 15:
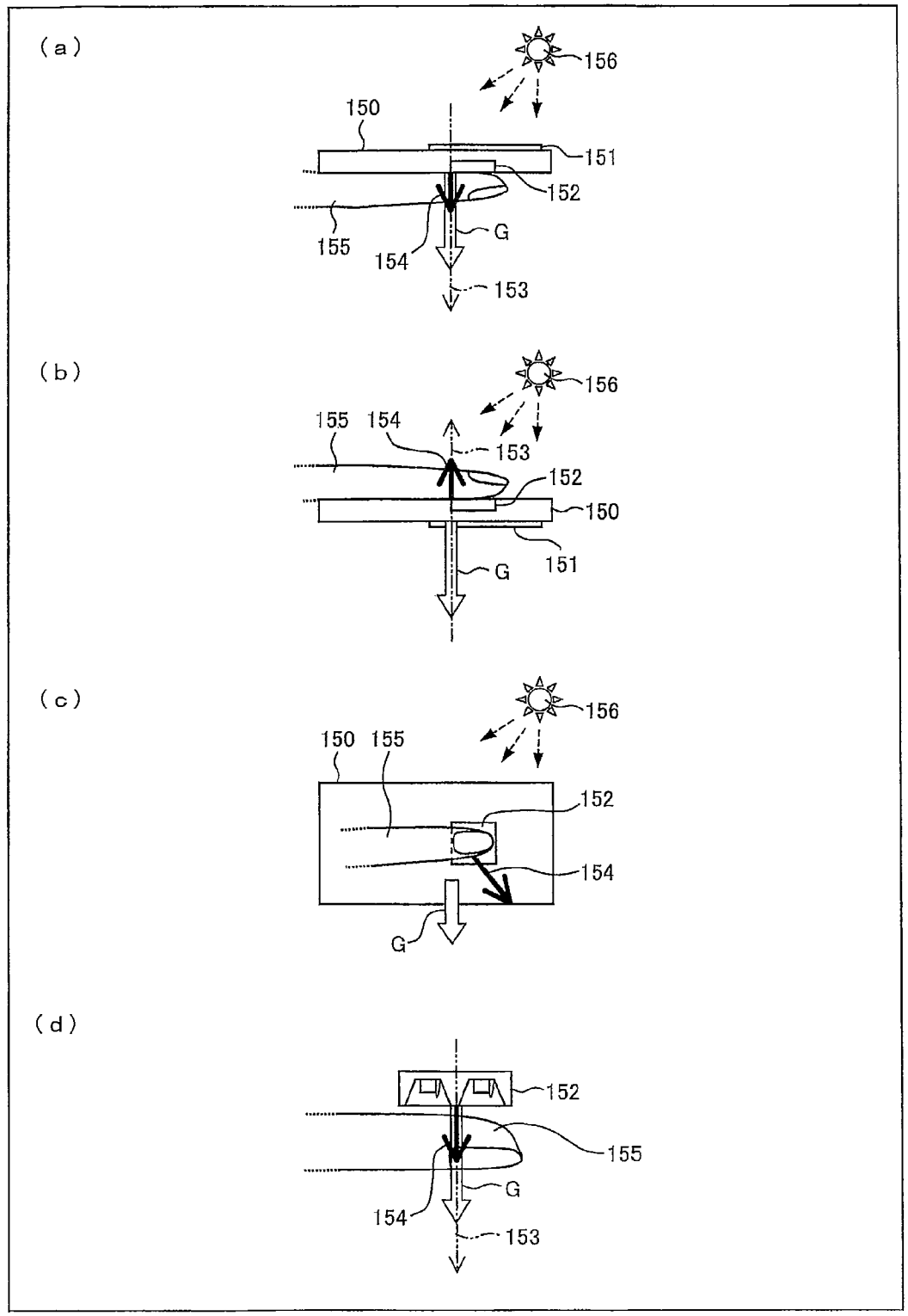

(a), (b), (c), and (d) of FIG. 15 are views illustrating conditions required for accurate pulse measurement in the seventh embodiment.

FIG. 16

Figure 16:
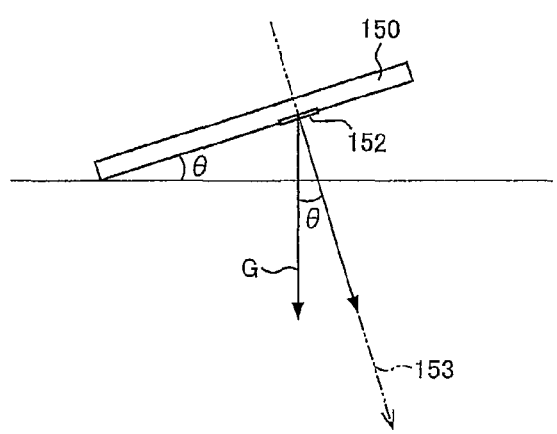
Figure 16:
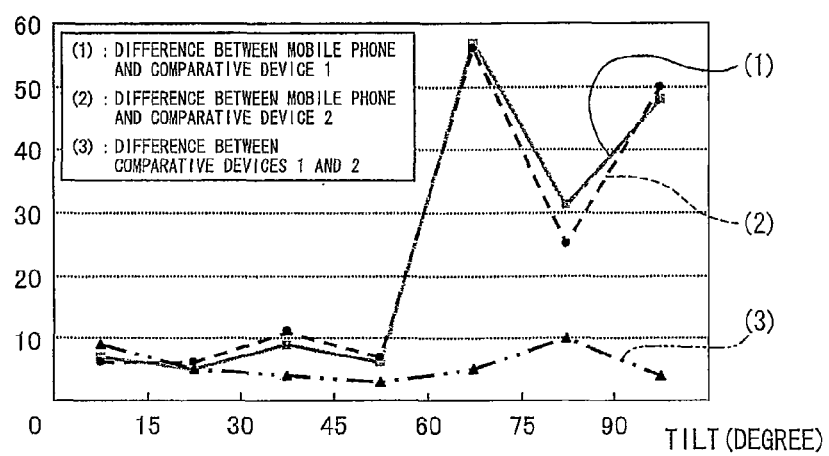

(a) and (b) of FIG. 16 are a view and a graph for explaining conditions required for accurate pulse measurement in the seventh embodiment.

FIG. 17

Figure 17:
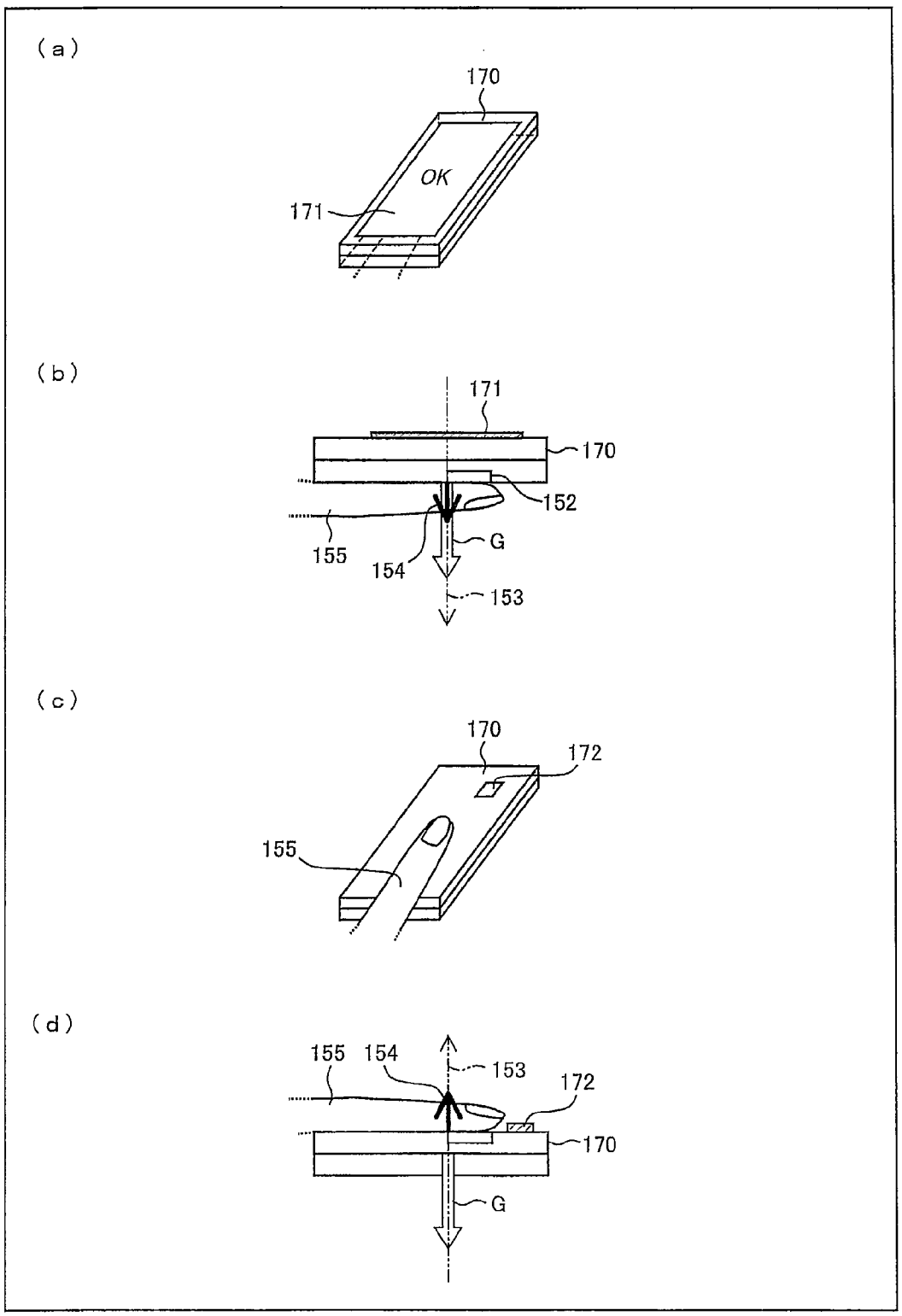

(a), (b), (c), and (d) of FIG. 17 are views for explaining states of pulse measurement in which a slidable mobile phone is used.

FIG. 18

Figure 18:
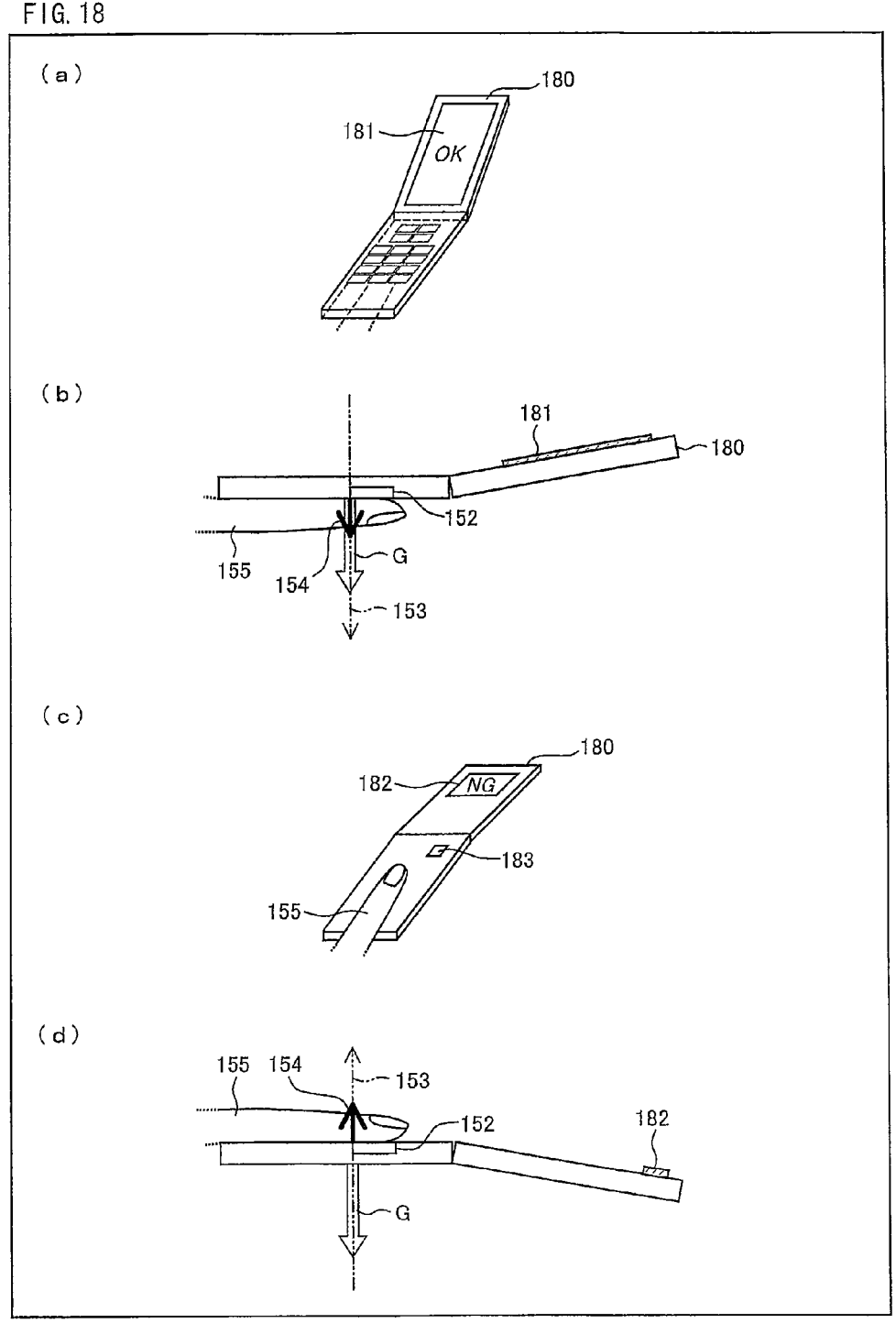

(a), (b), (c), and (d) of FIG. 18 are views for explaining states of pulse measurement in which a foldable mobile phone is used in a unfolded state.

FIG. 19

Figure 19:
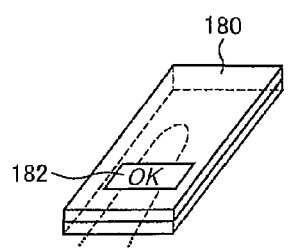
Figure 19:
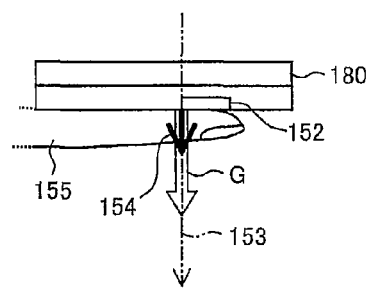
Figure 19:
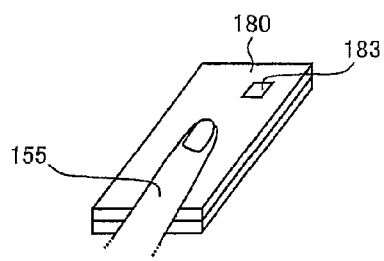
Figure 19:
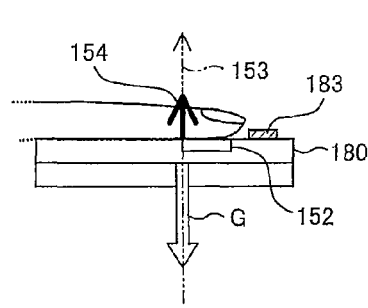

(a), (b), (c), and (d) of FIG. 19 are views for explaining states of pulse measurement in which the foldable mobile phone is used in a folded state.

FIG. 20

Figure 20:
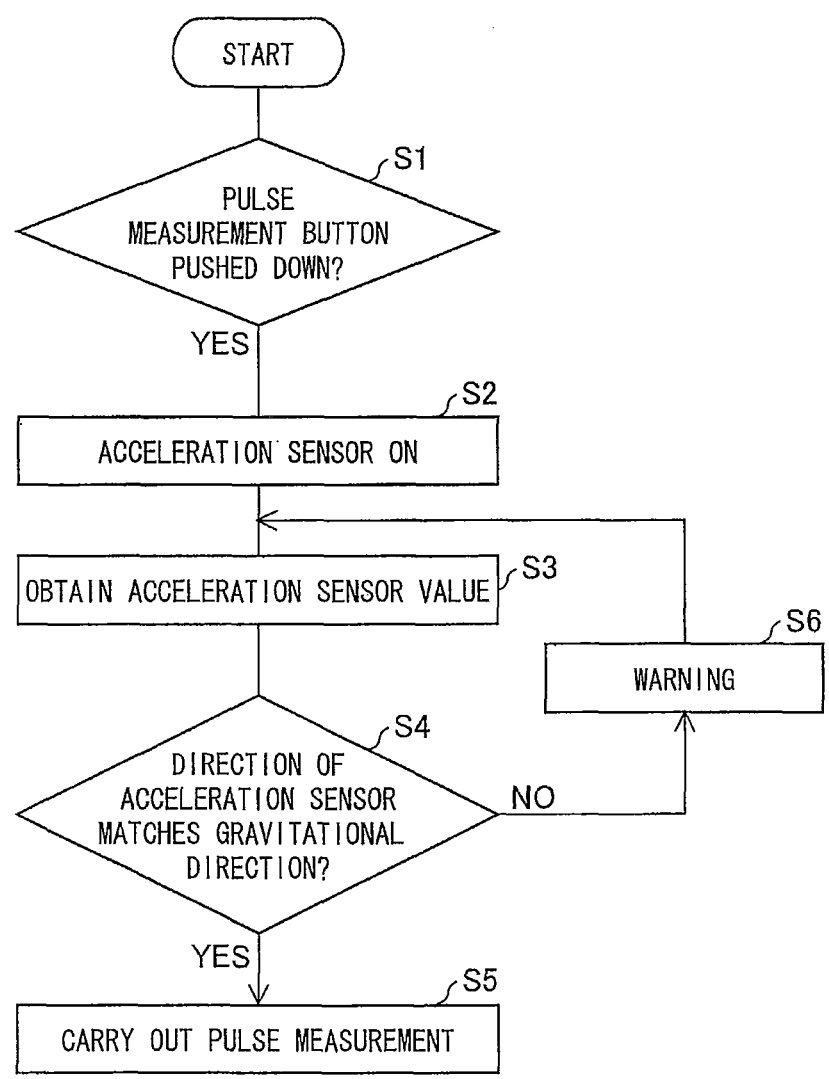

FIG. 20 is a view showing a first pulse measurement flow for detecting whether or not the mobile device is held in a proper attitude for pulse measurement.

FIG. 21

Figure 21:
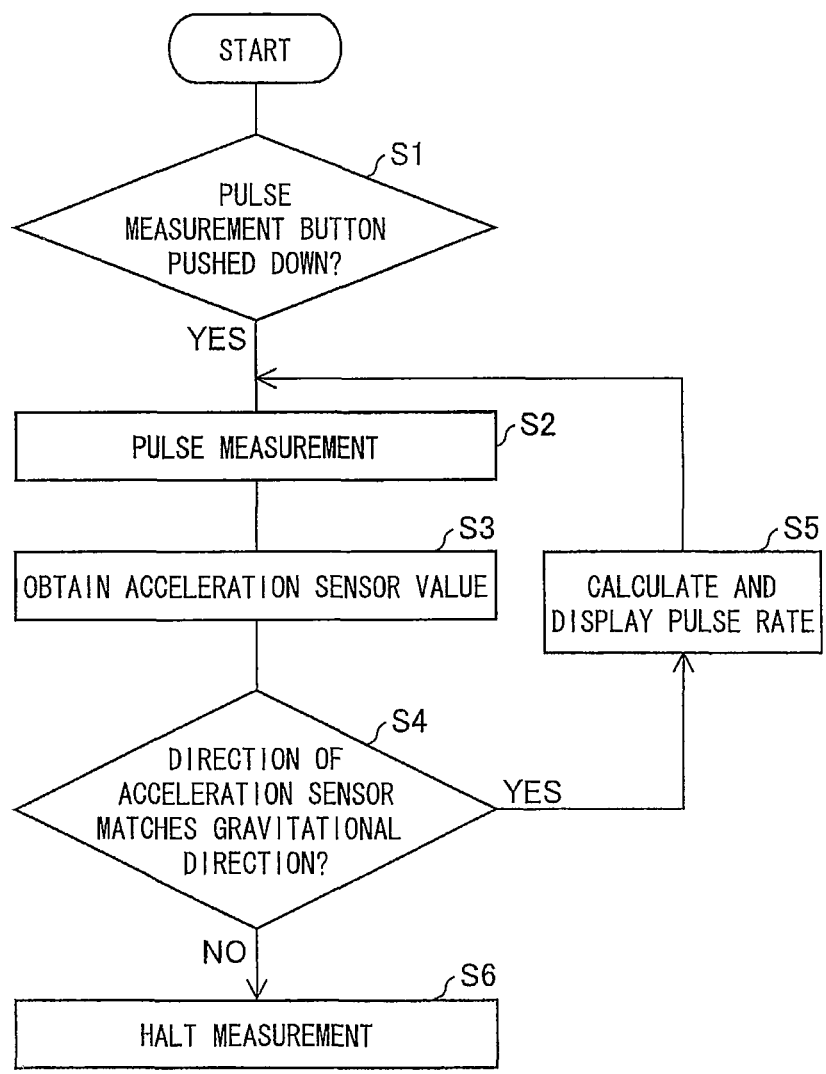

FIG. 21 is a view showing a second pulse measurement flow for detecting whether or not the mobile device is held in a proper attitude for pulse measurement.

FIG. 22

Figure 22:
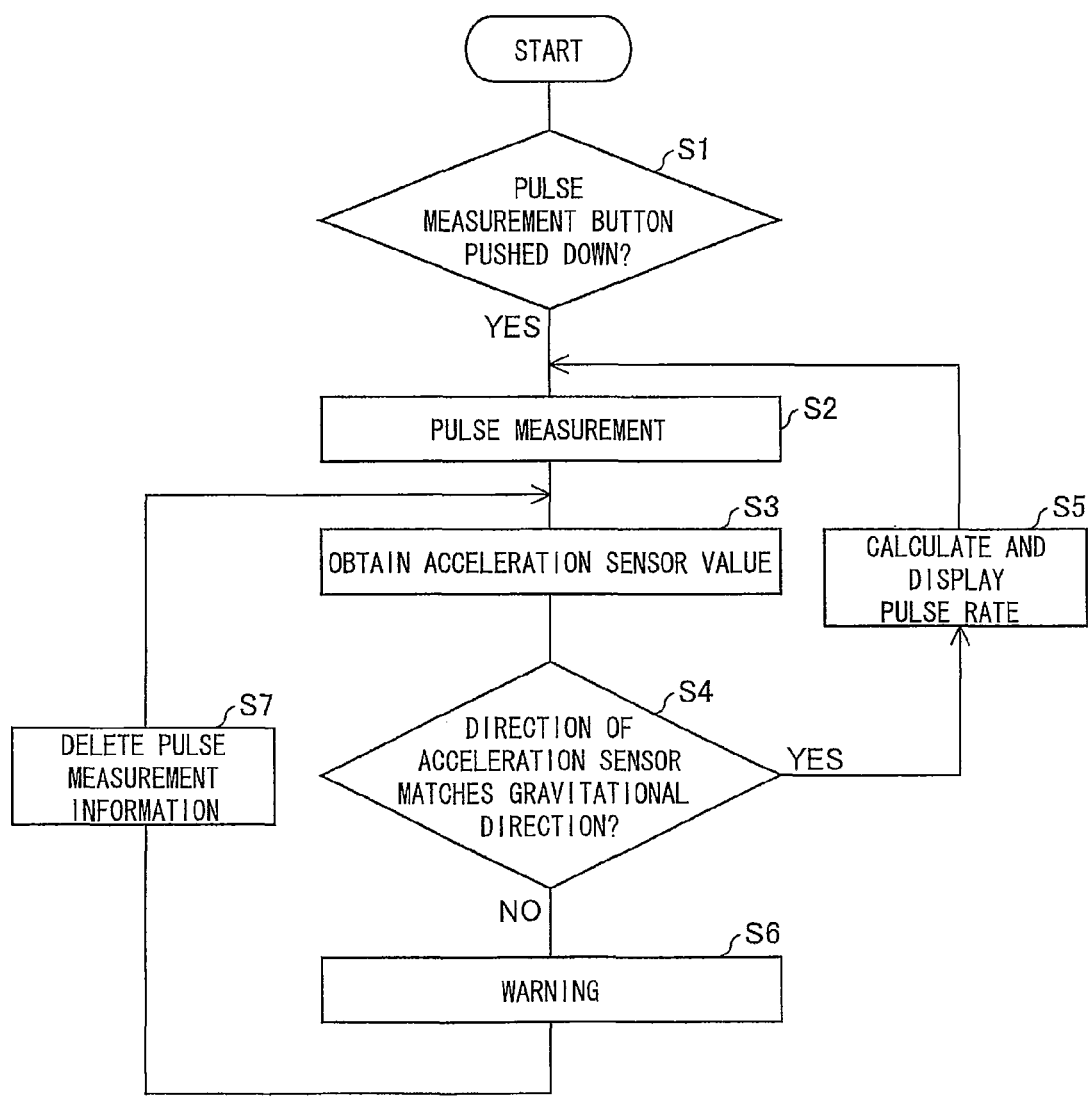

FIG. 22 is a view showing a third pulse measurement flow for detecting whether or not the mobile device is held in a proper attitude for pulse measurement.

FIG. 23

Figure 23:
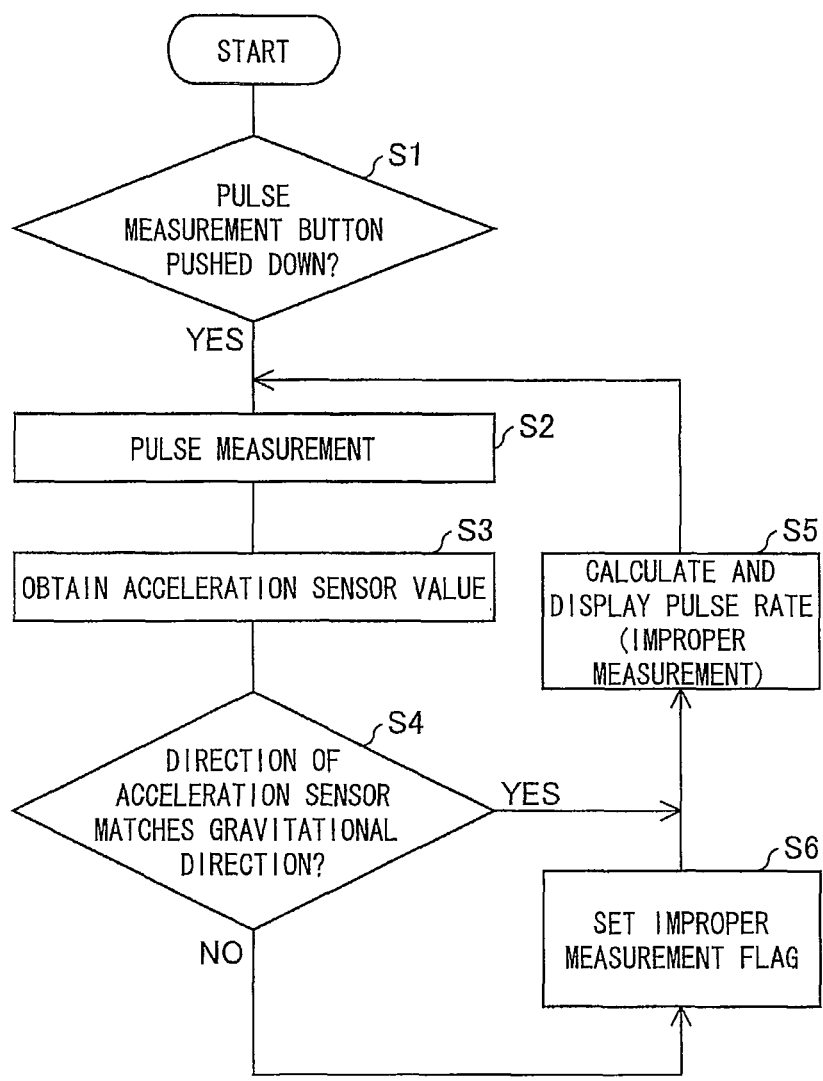

FIG. 23 is a view showing a forth pulse measurement flow for detecting whether or not the mobile device is held in a proper attitude for pulse measurement.

FIG. 24

Figure 24:
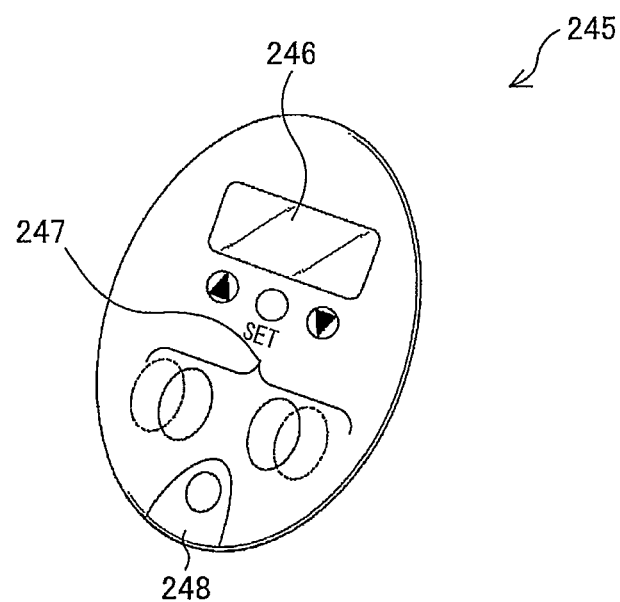

FIG. 24 is a view illustrating an arrangement of a conventional pulse meter.

FIG. 25

Figure 25:
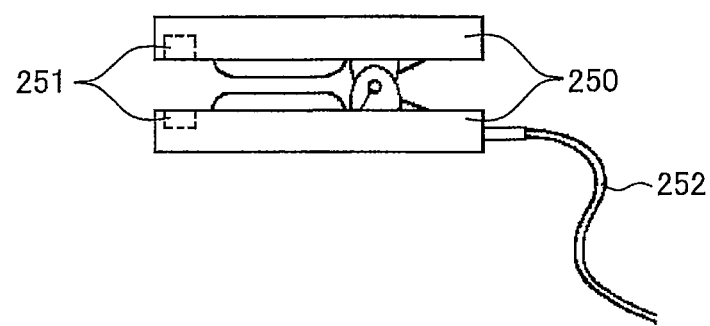

FIG. 25 is a view illustrating a sensor section of the conventional pulse meter.

DESCRIPTION OF EMBODIMENTS

Before describing embodiments of the present invention, the following first shows, with reference to FIGS. 4 and 5, an overview of a pulse meter having a pulse sensor constituted by a light-emitting element and a light-receiving element, and then, the following describes, with reference to FIG. 6, conditions required for stable pulse measurement in which a pulse meter is used which has a pulse sensor constituted by a light-emitting element and a light-receiving element which pulse sensor was invented by the inventors of the present invention.

FIG. 4 is a schematic view illustrating (i) an arrangement of a pulse sensor constituted by a light-emitting element and a light-receiving element, and (ii) a fingertip position where a pulse rate is measured by the pulse sensor. In FIG. 4, 40 indicates the sensor section, i.e., the whole pulse sensor constituted by the light-emitting element and the light-receiving element. The sensor section 40 includes a casing 41, and a light-emitting element and a light-receiving element 43 which are housed in the casing 41. The light-emitting element 42 is realized by an element such as a light-emitting diode which emits infrared rays. The light-receiving element 43 is realized by an element such as a phototransistor. FIG. 4 does not show an actual dimensional relation between the sensor section 40 and a fingertip 44 but merely shows a schematic view thereof. Further, FIG. 4 does not limit how the light-emitting element 42, the light-receiving element 43, and the fingertip 44 are disposed. Therefore, there can be various modifications such as an arrangement in which the light-emitting element 42 and the light-receiving element 43 are interchanged. Further, FIG. 4 does not show an actual dimensional relation between the light-emitting element 42 and the light-receiving element 43 in the sensor section 40. The sensor section 40 can be realized by an optical sensor which is a so-called reflective photointerrupter.

In the measurement of a pulse rate, the fingertip 44 is placed on a top surface of the sensor section 40 so that infrared rays emitted from the light-emitting element 42 toward the fingertip 44 may be reflected by the fingertip 44 and then received by the light-receiving element 43. A blood flow volume in a blood vessel and an amount of blood hemoglobin change in response to a heartbeat. The change is detected by the light-receiving element 43 as a change in amount of reflected infrared rays.

FIG. 5 is a view illustrating an overview of a control section which calculates a pulse rate on the basis of an output from the sensor section 40. In FIG. 5, 50 indicates the whole of a control section 50. The control section 50 includes a data obtaining section 51 for receiving data from the sensor section 40, and a pulse rate calculating section 52 for calculating a pulse rate on the basis of the data received via the data obtaining section 51. The pulse rate calculating section 52 calculates a pulse rate on the basis of the data from the sensor section 40. Upon fixing the pulse rate, the pulse rate calculating section 52 notifies a user, via a notification section 53, that the pulse rate is fixed. Further, the pulse rate thus found is displayed by the display section 53. The notification section 53 is constituted by an LED, a vibrator, etc. The notification section 53 carries out the notification visually, aurally, or haptically. Since calculating a pulse rate on the basis of the data from the sensor section 40 is publicly known, the following omits to describe the details thereof.

The following describes conditions required for easy and stable pulse measurement in which a pulse meter is used which has an optical sensor constituted by a light-emitting element and a light-receiving element which optical sensor was invented by the inventors of the present invention.

FIG. 6 is a figure showing results of pulse measurement performed by the sensor section 40 of FIG. 4 in which pulse measurement a force between the fingertip 44 and the sensor section 40 was variously changed. Specifically, FIG. 6 shows graphs of pulse waves, for the following forces between the fingertip 44 and the sensor section 40: 10 gf, 30 gf, 50 gf, 100 gf, 150 gf, 200 gf, 250 gf, and 300 gf. In each of the graphs, the horizontal axis represents second-scale time whereas the vertical axis represents output voltages from the light-receiving element of the sensor section 40. More specifically, the vertical axis represents, as the output voltages from the light-receiving element, characteristic data values from 0 to −4095 into which the output voltages are converted by an AD converter.

The graph corresponding to 100 gf shows that a highly stable pulse wave output can be obtained. The pulse wave output corresponds to changes in blood flow volume in a blood vessel which changes are caused in accordance with heartbeats. A pulse rate can be measured by counting the number of peaks of the pulse wave output per minute. In a case where such a stable pulse wave output can be obtained, an accurate pulse rate can be obtained in such a manner that a user touches the sensor section 40 with the fingertip 44 usually for a time period from about 3 to 10 seconds. According to the graph corresponding to 150 gf, waveforms of the pulse wave output are slightly smaller than those corresponding to 100 gf. However, the pulse wave output is stable as in the case of 100 gf. Thus, it is possible to measure a stable and accurate pulse rate.

In contrast, according to the graph corresponding to 10 gf, the pulse wave output is considerably unstable, and hardly corresponds to pulses. It is impossible to obtain a pulse rate from such a pulse wave output. In the case of 30 gf, the pulse wave output somewhat corresponds to pulses. However, the pulse wave output is not stable as a whole. It was impossible to obtain an accurate pulse rate from the pulse wave output.

According to the graph corresponding to 50 gf, the pulse wave output is stable, except that its initial part (in a period from 0 to 2 seconds) is unstable. In this case, a time required until a measurement result is obtained slightly varies depending on users. In addition, some additional time is required until a measurement result is obtained, as compared to the case of 100 gf. However, the pulse measurement itself was possible. According to the graph corresponding to 200 gf, the peaks of the pulse wave output are lower than those corresponding to 150 gf. Furthermore, the pulse wave output is unstable in its intermediate part (in a period from 5 to 8 seconds). However, the pulse measurement itself was also possible, as in the case of 50 gf.

The force between the fingertip 44 and the sensor section 40 was further increased to 250 gf. This resulted in a pulse wave output having a further lowered shape. Furthermore, the pulse wave output became more unstable. As a result, accurate pulse measurement was no longer possible. In the case of 300 gf, it was almost impossible to distinguish pulses on the basis of the pulse wave output, as evidently shown in the graph.

When an object having a certain weight is put on the fingertip 44, the weight merely acts on the fingertip 44 in principle. Therefore, the force itself acting on the fingertip 44 cannot vary. However, in actuality, how the mobile terminal is supported by a user changes due to a factor such as a small shake of the fingertip 44. Thus, the force acting on the fingertip 44 varies accordingly. In case where the force acting on the fingertip 44 is small, the change in the force greatly affects pulse measurement. An experiment conducted by the inventors of the present invention showed that pulse measurement was impossible in terms of practicality in the case of a force of less than 50 gf. On the other hand, a too large force acting on the fingertip 44 disturbs a blood flow in a blood vessel. This makes it impossible to measure a pulse rate.

As described above, the experiment conducted by the inventors of the present invention showed that pulse measurement was impossible in terms of practicality in the case of a force of less than 50 gf or of more than 200 gf although in a range from 50 gf to 200 gf, it was possible to measure a pulse rate easily and accurately in a short time, without a need such as special proficiency to the pulse meter. In addition, as is evident from the graphs, a highly stable pulse wave output can be obtained from the sensor section 40, provided that a force acting on the fingertip 44 falls particularly within a range from 100 gf to 150 gf. In this case, it was possible to measure a pulse rate more easily and more accurately in a shorter time.

This is attributed to the following facts. First, even if how the mobile terminal is supported changes due to a factor such as a movement of the fingertip 44, a force of 100 gf acting on the fingertip 44 rarely decreases to a force of less than 50 gf. Second, even if how the mobile terminal is supported changes due to a factor such as a movement of the fingertip 44, a force of 150 gf acting on the fingertip 44 rarely increases to a force of more than 200 gf.

The present invention was made in view of: those aforementioned conditions required for easy and accurate pulse measurement which were found by the inventors of the present invention; and further, weights of mobile terminals typified by mobile phones that users always carry with themselves. The present invention provides a mobile terminal having a pulse meter which mobile terminal has a sensor in its specific position and utilize a weight of the mobile terminal itself so as to measure a pulse rate easily and accurately in a short time.

[First Embodiment]

The following describes a first embodiment according to the present invention. Although the following contains various limitations preferable for carrying out the present invention, a technical scope of the present invention is not limited to the following embodiment and drawings.

FIG. 1 is a view illustrating one example of that mobile terminal having a pulse meter which is realized in accordance with the present invention. FIG. 1 illustrates an example in which a foldable mobile phone is especially adopted as the mobile terminal. Both (a) and (b) of FIG. 1 are perspective views illustrating an unfolded state of the foldable mobile phone. (a) of FIG. 1 is a view of a front side of the foldable mobile phone whereas (b) of FIG. 1 is a view of a back side thereof.

In each of (a) and (b) of FIG. 1, 10 indicates the whole of a foldable mobile phone 10. The mobile phone 10 includes a first casing 1, a second casing 2, and a joint 3 for foldably joining the first casing 1 with the second casing 2.

Provided on an inner surface of the first casing 1 (i.e., surface which makes contact with the second casing 2 when the mobile phone 10 is folded) are (i) a first display section 4 constituted by a liquid crystal display apparatus etc., and (ii) a speaker 9 to be used when the mobile phone 10 is used as a mobile phone. Provided on an outer surface of the first casing 1 are (i) a second display section 5 similarly constituted by a liquid crystal display apparatus etc., (ii) a camera 11 for taking a photograph, and (iii) operation keys 12. The operation keys 12 mainly serve as an operation section in use of the camera 11. Functions of the operation keys 12 can be switched to different functions including a function of the pulse meter of the present invention so that the operation keys 12 can also serve as an operation section for executing the different functions.

Provided on an inner surface of the second casing 2 (i.e., surface which makes contact with the first casing 1 when the mobile phone 10 is folded) are (i) input keys 6 and (ii) various operation keys 7, which are provided as those of an operation section required in use of the mobile phone 10 as a mobile phone, and (iii) a microphone 8. As is the case with the operation keys 12, functions of the input keys 6 and the operation keys 7 can be switched to different functions so that the input keys 6 and the operation keys 7 can be used in an operation for, e.g., pulse measurement. According to the present invention, a sensor 15 is further provided to an upper end portion of the outer surface of the second casing 2, i.e., provided to an end portion thereof close to the joint 3. The sensor 15 is constituted by a light-emitting element and a light-receiving element which are for pulse detection. The sensor 15 can be realized by an optical sensor referred to as reflective photointerrupter.

As is evident from (b) of FIG. 1, the sensor 15 is provided to a planar part of the upper end portion of the second casing 2. When a fingertip makes contact with the sensor 15, this arrangement allows easy haptic recognition of how the mobile phone 10 is supported, i.e., of how the mobile phone 10 tilts. This makes it possible to suppress that fluctuation of a weight acting on the fingertip which is caused by the tilt, in a case where the mobile phone 10 is supported substantially horizontally in pulse measurement as described later with reference to FIGS. 2 and 3.

FIG. 2 is a schematic view illustrating an overview of pulse measurement in which the foldable mobile phone 10 of FIG. 1 having the pulse meter is used. (a) of FIG. 2 illustrates an unfolded state of use of the foldable mobile phone 10. This usage is preferred in a case where the mobile phone 10 is relatively light. (b) of FIG. 2 illustrates a folded state of use of the foldable mobile phone 10. This usage is preferred in a case where the mobile phone 10 is heavy. In each of (a) and (b) of FIG. 2, members also illustrated in FIG. 1 are indicated by the common reference signs, and the following does not repeat descriptions of such members. Any of (a) and (b) of FIG. 2 shows that the sensor 15 is provided to the tip section of the second casing 2, i.e., provided in a position close to the joint 3.

In the unfolded state of use of the foldable mobile phone 10, a palm supports the mobile phone 10 from below at the point A in an lower end portion of the outer surface of the second casing 2, and a fingertip 24 supports, from below, the sensor 15 provided in the point B in the upper end portion of the outer surface of the second casing 2, as illustrated in (a) of FIG. 2. Specifically, the fingertip 24 makes contact with the sensor 15 from below so as to support the foldable mobile phone 10 substantially horizontally. In a case where the first casing 1 and the second casing 2 have substantially the same weight in the unfolded state, a barycentric position of the foldable mobile phone 10 is the center position C.

Accordingly, in a case where the sensor 15 is provided in the center position C, the fingertip 24 supports substantially the total weight of the foldable mobile phone 10. It follows that a force acting between the fingertip 24 and the sensor 15 substantially corresponds to the total weight of the foldable mobile phone 10. Furthermore, the total weight of the foldable mobile phone 10 merely acts on the fingertip 24 unlike in a case where a user presses his fingertip against the sensor 15 on his own will. Therefore, the fluctuation of the force acting between the fingertip 24 and the sensor 15 is ideally zero. Further, how the foldable mobile phone 10 is supported in the pulse measurement is hardly different from how the foldable mobile phone 10 is supported in reading or creating an e-mail. Therefore, there is no need such as special proficiency.

It is necessary to hold the foldable mobile phone 10 in a constant state for a while until a pulse measurement result is obtained. That supported state in the pulse measurement which is hardly different from the supported state in use of the foldable mobile phone 10 as a mobile phone is a highly important factor in that anyone can use the foldable mobile phone 10. In particular, the factor is important when assuming that elderly people account for a high proportion of users of the pulse meter. As described above with reference to FIG. 5, it is preferably arranged such that the pulse rate calculating section 52 calculates a pulse rate on the basis of the data received from the sensor 15, and upon fixing the pulse rate, the pulse rate calculating section 52 notifies a user, via a beeper or the like, that the pulse rate is fixed. It can also be arranged such that discontinuous beep sounds are generated in sync with pulses in a case where the pulse meter normally operates in pulse measurement. This makes it possible to give a user a sense of reassurance that the pulse measurement is surely performed.

Currently, foldable mobile phones each usually have a weight from approximately 100 g to 150 g. If a full weight of a foldable mobile phone in this weight range acts on the fingertip 24, the weight falls in the range of forces necessary for stable pulse measurement which weight range is described above with reference to FIG. 6. Accordingly, providing the sensor 15 of the pulse meter in the vicinity of the joint 3 of a foldable mobile phone allows many foldable mobile phones to perform stable pulse measurement.

In a case where a sensor 16 indicated with the dashed line is provided in a position closer to the point A than the barycentric position C instead of the sensor 15, it is necessary to hold the foldable mobile phone 10 so as to pinch the end portion thereof on a point A side, in order to prevent the end portion from moving upward. However, the arrangement makes it possible to apply a heavier weight to the fingertip 24 at the point B. Thus, in a case where the foldable mobile phone 10 has a light weight, it is possible to adjust a weight acting on the fingertip 24 within a certain weight range, by adjusting the position of the sensor 15, although there is a limit.

The above deals with a case where the foldable mobile phone 10 has a weight from 100 g to 150 g. However, even if the weight does not fall within this range, it is possible to apply, to the fingertip 24, a force in the range from 50 gf to 200 gf, provided that the foldable mobile phone 10 has a weight within the range from 50 g to 200 g, as is described with reference to FIG. 6. Therefore, providing the sensor 15 in the vicinity of the joint 3 solely makes it possible to provide that mobile terminal having a pulse meter which makes it possible to perform pulse measurement easily and accurately in a short time.

In use of the pulse meter, as described above, the mobile terminal is put on a palm of a user so that the user may touch, with his fingertip, that sensor 15 provided on the back side of the mobile terminal which has the light-receiving element. This makes an effect of external light relatively small. As a result, accurate measurement is realized. Furthermore, an arrangement in which an exposed area of the sensor 15 has a size within, e.g., 1 cm so as to be smaller than the fingertip 24 allows the fingertip 24 to cover the entire surface of the sensor 15 in pulse measurement. This makes the effect of external light further small.

In this case, the user has a difficulty in knowing where to touch with his fingertip since the sensor 15 is provided on the back side of the mobile terminal. Therefore, a fingertip guide for guiding a fingertip is preferably provided in the vicinity of the sensor 15, although this is not illustrated. The fingertip guide can be realized by a protrusion, a depressed portion, or the like, which is provided in the vicinity of the sensor 15, or provided along the whole circumference of the sensor 15 or along a part of the whole circumference. A portion made from a material with a different hand feeling can be provided instead of the projection and the depressed portion.

The mobile terminal makes it possible to store pulse data. Therefore, analysis of long-term pulse data allows highly detailed health management. Further, in a case where the first display section 4 displays operating instructions of the pulse meter, a user can view the operating instructions while operating the pulse meter by using the keys provided on the main body. This allows anyone to easily measure a pulse rate.

A foldable mobile phone or the like which has a large liquid crystal screen and has a relatively heavy total weight of greater than 200 g can be designed so as to be used as a pulse meter in the folded state. (b) of FIG. 2 illustrates such an example. In (b) of FIG. 2, the sensor 15 is provided closer to the barycentric position C in the folded state than the position of the sensor 15 in (a) of FIG. 2. This arrangement is a result of consideration made so that as much weight of the foldable mobile phone 10 as possible may be applied to the fingertip 24 at the point B. Needless to say, e.g. the sensor 17 indicated with the dashed line can be provided instead of the sensor 15, provided that a force acting on the fingertip 24 can be determined so as to fall within the range from 50 gf to 200 gf.

A force acting between the fingertip 24 and the sensor 15 can be adjusted to a desired value by adjusting relations among: the weight of the foldable mobile phone 10; a distance "a" between the point A and the point B; and a distance "b" between the point A and the barycentric position C of the foldable mobile phone 10. In a case where the distance "a" is twice the distance "b" and the foldable mobile phone 10 has a total weight of 200 g, a force of approximately 100 gf acts on the fingertip 24. The force satisfies that condition required for stable pulse measurement which is described above with reference to FIG. 6. In any case, the force acting on the fingertip 24 has a constant value to be determined by the weight of the mobile terminal. The fluctuation of the force is ideally zero unlike in a case where a user presses his fingertip against the sensor 15 on his own will.

The example above deals with a case where the mobile terminal particularly has a weight of 200 g. However, needless to say, the present invention is not limited to this but is usable, provided that a force acting between the fingertip 24 and the sensor 15 falls within the range from 50 gf to 200 gf, as is described above with reference to FIG. 6. Further, as described with reference to FIG. 6, it is more preferable to adjust the position of the sensor 15 so as to determine the force acting on the fingertip 24 within the range from 100 gf to 150 gf.

FIG. 3 is a schematic view illustrating an actual pulse measurement in which that foldable mobile phone 10 having a pulse meter which is realized in accordance with the present invention. (a) and (b) of FIG. 3 illustrate the unfolded state of use. (a) of FIG. 3 illustrates the front side of the foldable mobile phone 10 whereas (b) of FIG. 3 illustrates the back side thereof. (c) of FIG. 3 illustrates the folded state of use. In each of (a), (b), and (c) of FIG. 3, members also illustrated in FIG. 1 are indicated by the common reference signs, and the following does not repeat descriptions of such members.

As is evident from (b) of FIG. 3, it is necessary to touch the sensor 15 with the fingertip 24 in pulse measurement. Further, as illustrated in (a) of FIG. 3, the foldable mobile phone 10 is preferably supported at the following two points: (i) the point A and (ii) the fingertip 24 touching the sensor 15. As is evident from (a) of FIG. 3, the way of holding is actually almost the same as the way that the foldable mobile phone 10 is used to execute a function such as the e-mail function. Therefore, there is no need such as special proficiency to the pulse meter. The pulse meter is operated via the input keys 6. The measured result is displayed on the first display section 4. Further, as is described above with reference to FIG. 5, it is preferable to notify, by generating discontinuous beep sounds in sync with pulses in pulse measurement, a user that the pulse meter normally operates. Further, when a measurement result is fixed, it is preferable to notify, by an appropriate method, a user that the measurement result is fixed.

As is illustrated in (c) of FIG. 3, pulse measurement is performed also in the folded state of use in such a manner that a user touches, with the fingertip 24, the sensor 15 (not illustrated) provided on the back side of the foldable mobile phone 10, and holds the end portion thereof on the point A side. The pulse meter is operated by the operation keys 12. The measured result is displayed on the second display section 5. Also in this case, the way of holding is almost the same as the way that a user views the second display section 5 in the folded state. Therefore, there is no need such as special proficiency to the pulse meter.

[Second Embodiment]

The following describes a second embodiment of the present invention. Although the following contains various limitations preferable for carrying out the present invention as is the case with the first embodiment, a technical scope of the present invention is not limited to the following embodiment and drawings.

FIGS. 7 and 8 are views for describing the second embodiment of the present invention. FIGS. 7 and 8 specifically illustrate an example in which a straight-type mobile phone is adopted as a mobile terminal. (a) of FIG. 7 illustrates a front side of the straight-type mobile phone whereas (b) of FIG. 7 illustrates a back side thereof. In each of (a) and (b) of FIG. 7, 70 indicates the whole of a straight-type mobile phone 70. Provided on the front side of the straight-type mobile phone 70 are a display section 74 and keys 76 to be used as an operation section. Provided to an upper end portion of the back side of the straight-type mobile phone 70 is a sensor 75 for a pulse meter in which sensor 75 a reflective photointerrupter is used. In addition, a microphone, a speaker, etc. which are necessary for a mobile phone are also provided although not illustrated.

FIG. 8 is a view schematically illustrating pulse measurement in which the straight-type mobile phone 70 having a pulse meter is used. The pulse measurement is performed in almost the same manner as the folded state of use of the foldable mobile phone 10 in (b) of FIG. 2. However, a straight-type mobile phone has a high degree of freedom of a position where the sensor 75 is provided, for the reason that a straight-type mobile phone is usually longer than a foldable mobile phone in the folded state. That is, it is possible to arrange such that the sensor 75 is provided much closer to the barycentric position C, without causing any difficulty in holding the straight-type mobile phone 70 in pulse measurement. By contriving a layout of internal components of the straight-type mobile phone 70 so that the barycentric position C comes as close as possible to the end portion to which the sensor 75 is provided, it is possible to provide the sensor 75 closer to the end portion. This allows a user to easily hold the straight-type mobile phone 70 in pulse measurement.

Also in the second embodiment, a force acting on the fingertip 24 touching the sensor 75 is adjusted to a force from 50 gf to 200 gf, by adjusting relations among: the total weight of the straight-type mobile phone 70; a distance "a" from a point A on a lower end portion of the straight-type mobile phone 70 to the sensor 75; and a distance "b" from the point A to the barycentric position C. If the straight-type mobile phone 70 has a very light weight, the sensor 75 can be provided much closer to the point A than the barycentric position C. In this case, it is necessary to hold the lower end portion in order to prevent the lower end portion from moving upward. However, this results in a greater force acting on the sensor 75. Further, more stable pulse measurement can be realized by setting a force acting on the sensor 75 within a range from 100 gf to 150 gf in consideration of some fluctuation of the force as is the case with the foldable mobile phone 10. In addition, this makes it possible to measure a pulse rate more easily and more accurately in much shorter time.

[Third Embodiment]

The following describes a third embodiment of the present invention. Although the following contains various limitations preferable for carrying out the present invention as is the case with the first embodiment, a technical scope of the present invention is not limited to the following embodiment and drawings.

FIG. 9 illustrates an example in which the present invention is applied to a slidable mobile phone. In FIG. 9, 91 indicates a first casing 91 constituting a main body of the slidable mobile phone. Similarly, 92 indicates a second casing 92 constituting the main body. The first casing 91 and the second casing 92 are joined to each other so as to overlap each other and slide in the directions indicated with the arrow A, as illustrated in FIG. 9. A display section 94 is provided on the first casing 91. Keys 93 are provided as an operation section on an upper surface of the second casing 92.

Further, in accordance with the present invention, a sensor for a pulse meter is provided to a front end portion 95 on a back side of the second casing 92 although the sensor is hidden behind the second casing 92 in FIG. 9. The position of the sensor is adjusted so that a force acting on the sensor may fall within the range from 50 gf to 200 gf in a case where in pulse measurement, the slidable mobile phone is supported from below at the sensor and a rear end portion 96 of the second casing 92. In a case where the force particularly falls with the range from 100 gf to 150 gf, a much better measurement result can be obtained. The sensor comes close to the barycentric position of the slidable mobile phone when, as illustrated in FIG. 9, the first casing 91 is slid out so that the slidable mobile phone may have a longer whole length. Therefore, the arrangement can be applied to a mobile phone having a relatively light weight. On the other hand, in a case where the arrangement is applied to a mobile phone having a heavy weight, the mobile phone is designed so that the first casing 91 may not slid out in pulse measurement, as is the case with the folded state of use of the foldable mobile phone 10 described with reference to (b) of FIG. 2.

[Fourth Embodiment]

The following describes a fourth embodiment of the present invention. Although the following contains various limitations preferable for carrying out the present invention as is the case with the first embodiment, a technical scope of the present invention is not limited to the following embodiment and drawings.

FIG. 10 illustrates an example in which the present invention is applied to a biaxial hinge-type mobile phone. In FIG. 10, 101 indicates a first casing 101 constituting a main body of the biaxial hinge-type mobile phone. Similarly, 102 indicates a second casing 102 constituting the main body. The first casing 101 and the second casing 102 are joined to each other via a joint 103 which is referred to as biaxial hinge. The joint 103 can be rotated around the axis 105 in the directions indicated with the arrow A, and in addition, can be rotated around the axis 106 perpendicular to the axis 105 in the directions indicated with the arrow B. 104 indicates a display section 104 provided to the first casing 101.

As is the case with a common foldable mobile phone, the biaxial hinge-type mobile phone can be folded so that the display section 104 may face the second casing 102, or can be folded so that the display section 104 may face upward. Further, as in the case of FIG. 1, the biaxial hinge-type mobile phone can be used in the unfolded state so that the display section 104 and the operation section 109 may face upward.

In accordance with the present invention, a sensor for a pulse meter is provided to a front end portion 107 on a back side of the second casing 102 although the sensor is hidden behind the second casing 102 in FIG. 10. The position of the sensor is adjusted so that a force acting on the sensor may fall within the range from 50 gf to 200 gf in a case where in pulse measurement, the biaxial hinge-type mobile phone is supported from below at the sensor and a rear end portion 108 of the second casing 102. In a case where the force particularly falls with the range from 100 gf to 150 gf, a much better measurement result can be obtained.

In a case where the arrangement is applied to a mobile phone having a light weight, the position of the sensor is determined so that pulse measurement may be performed in the unfolded state as illustrated in FIG. 1. In contrast, in a case where the arrangement is applied to a mobile phone having a relatively heavy weight, the position of the sensor is determined so that the pulse measurement may be performed in the folded state.

[Fifth Embodiment]

The following describes a fifth embodiment of the present invention. Although the following contains various limitations preferable for carrying out the present invention as is the case with the first embodiment, a technical scope of the present invention is not limited to the following embodiment and drawings.

FIG. 11 illustrates an example in which the present invention is applied to a mobile phone whose display section itself can be rotated. In FIG. 11, 111 indicates a first casing 111 constituting a main body of the mobile phone of the present embodiment. Similarly, 112 indicates a second casing 112 constituting the main body. As is the case with the foldable mobile phone 10, the first casing 111 and the second casing 112 can be rotated around the axis 115 in the directions indicated with the arrow A.

In the present embodiment, a third casing 113 is further provided on the first casing 111 so as to be rotatable in the directions indicated by the arrow B. The main body of the mobile phone is constituted by the first casing 111, the second casing 112, and the third casing 113.

A display section 114 is provided to the third casing 113. The display section 114 can be used in a portrait-orientation in which the display section 114 is disposed lengthwise on the first casing 111. Alternatively, the display section 114 can be used in a landscape-orientation in which the display section 114 is disposed laterally on the first casing 111. The mobile phone is usually used in the former state as a mobile phone. On the other hand, the mobile phone is used in the latter state in TV watching in which a TV function is utilized, in Internet browsing, etc.

In accordance with the present invention, a sensor for a pulse meter is provided to a front end portion 117 on a back side of the second casing 112 although the sensor is hidden behind the second casing 112 in FIG. 11. The position of the sensor is adjusted so that a force acting on the sensor may fall within the range from 50 gf to 200 gf in a case where in pulse measurement, the mobile phone is supported from below at the sensor and a rear end portion 118 of the second casing 112. In a case where the force particularly falls with the range from 100 gf to 150 gf, a much better measurement result can be obtained.

In a case where the arrangement is applied to a mobile phone having a light weight, the position of the sensor is determined on the assumption that the pulse measurement is performed in the unfolded state. On the other hand, in a case where the arrangement is applied to a mobile phone having a heavy weight, the position of the sensor is determined on the assumption that the pulse measurement is performed in the folded state

[Sixth Embodiment]

The following describes a sixth embodiment of the present invention, with reference to FIG. 12. Although the following contains various limitations preferable for carrying out the present invention as is the case with the first embodiment, a technical scope of the present invention is not limited to the following embodiment and drawings.

FIG. 12 is a block diagram showing a functional arrangement of the mobile terminal of the present invention. FIG. 12 shows an arrangement of the mobile terminal having various additional functions in addition to the mobile phone function.

In FIG. 12, 122 indicates a main control device 122 for controlling the whole mobile terminal of the present invention. The main control device 122 is realized by a microcomputer having a CPU. 121 indicates a wireless section for controlling transmission and reception of an electric wave in use of the mobile terminal as a mobile phone. 123 indicates a phone call control section for controlling a phone call also in use of the mobile terminal as a mobile phone. The wireless section 121 and the phone call control section 123 are used in use of the mobile terminal as a usual mobile phone, together with a speaker 124, a microphone 125, a display section 132, an operation input section 133, a data storing section 134, etc. Since how the mobile terminal operates as a mobile phone is well known, the following omits descriptions for these members.

The mobile terminal illustrated in FIG. 12 includes: a pulse obtaining section 128 having the pulse meter of the present invention; a camera section 120 constituted by a lens 127, a camera control section 126, etc.; a GPS section 129 having a well-known GPS receiver etc.; a pedometer section 130 having a well-known pedometer; and a TV receiving section 131 having an ordinary TV function and a TV telephone function.

Since concrete arrangements and operations of the camera section 120, the GPS section 129, the pedometer section 130, and the TV receiving section 131 are publicly known, the following omits details thereof. Each of the sections is controlled by the main control section 122. Each of the sections is operated via the operation input section 133. The display section 132 is used to display an operating state etc. of each of the sections.

The mobile terminal thus arranged allows a user to utilize a communication function of the mobile terminal so as to send, to: a healthcare provider such as a hospital; a personal computer in a home of the user; a mobile phone of a specific person; etc., pulse information containing a measured pulse rate and a waveform of a pulse wave such as those shown in FIG. 6. In a case where the pulse information is sent to a hospital or the like, the user can manage his exercise, in consultation with a medical doctor or the like. In a case where the pulse information is sent to a personal computer or the like, long-term data recording becomes very easy. This allows easy long-term health management.

In the present embodiment, the mobile terminal includes the pedometer section 130 and the GPS receiving section 129. The mobile terminal having these functions makes it possible to easily obtain: pulse information containing a pulse rate and pulse wave data such as those shown in FIG. 6; data indicative of the number of steps; position information; and date information. Therefore, By utilizing the communication function, useful information enriched with the information obtained via the mobile terminal can be sent to: a healthcare provider; a personal computer in the home of the user; a mobile phone of a specific person; etc.

For example, the user can send thereto "the number of steps and a pulse rate during walking (i.e., during exercise) in XX park on the date and time of YY" and "a pulse rate at home (i.e., during rest) on the date and time of ZZ." By correlating a pulse rate during rest with a pulse rate during exercise, it becomes possible to use the pulse rates to determine whether or not an exercise intensity is appropriate. An exercise intensity is a numeric value found as a percentage of an increase of a pulse rate during exercise from a pulse rate at rest. Details of the exercise intensity are omitted here. The exercise intensity is utilized in exercise management. In general, it is said that ideal exercise is started from an exercise intensity within a range from 50% to 60% and is taken at an exercise intensity of not higher than 70%. With the mobile terminal of the present invention, a user can manage his exercise in a detailed manner in consultation with a professional such as a medical doctor, in consideration of these exercise intensities.

In addition, the GPS function makes it possible to record detailed exercise history such as from where to where the user walked. This makes it possible to closely check an amount of exercise and also enjoy checking the exercise history. Such enjoyment motivates the user to regularly take exercise. Even if the mobile terminal does not have the GPS function but has only the pulse meter and the pedometer, such mobile terminal is still highly useful because the mobile terminal allows health management associated with the number of steps.

Adopting a three-dimensional acceleration sensor as a pedometer makes it possible to accurately measure the number of steps by just putting the mobile terminal in a pocket or a bag without paying attention to the attitude of the mobile terminal. Further, as described below in a seventh embodiment, the three-dimensional acceleration sensor can be used as an effective measure for accurate pulse measurement.

In the present embodiment, the mobile terminal includes the TV receiving section 131 which allows TV (television) watching and also has the TV telephone function. In this case, a user can send, in real time, pulse information to a terminal of a party while talking with the party by using the TV telephone function, so that the terminal of the party may display the pulse information. As described above, the sensor is provided on the back side of the mobile terminal. In addition, a user supports the back side from below so as to measure a pulse rate. Therefore, for example, two users watching the same broadcast program while talking by the mobile terminals can obtain each other's pulse information, thereby exchanging information such as "I am touched here!" In addition, the mobile terminal can be used in amusement such as finding a degree of compatibility between two users from a similarity of each other's pulse information. Needless to say, without using the TV telephone function, it is still possible to send pulse information to a party terminal so that the pulse information may be displayed thereon.

Thus, the present embodiment allows detailed exercise management utilizing an advice provided by a professional on the basis of exercise history. Furthermore, the present embodiment allows enjoyable exercise management with an element such as amusement. This is effective in motivating a user to regularly take exercise.

[Seventh Embodiment]

The following describes a seventh embodiment of the present invention, with reference to FIGS. 13 to 23. Although the following contains various limitations preferable for carrying out the present invention as is the case with the first embodiment, a technical scope of the present invention is not limited to the following embodiment and drawings.

FIG. 13 is a block diagram illustrating the seventh embodiment. FIG. 14 is a view schematically illustrating an overview of how a three-dimensional acceleration sensor used in the present embodiment operates. FIGS. 15 and 16 are views illustrating conditions required for accurate pulse measurement. FIGS. 17 to 19 are views illustrating states in which various types of mobile phones are used as pulse meters. FIGS. 20 to 23 are flowcharts of pulse measurement.

First, with reference to FIG. 15, the following describes pulse measurement utilizing a mobile device having a "pulse sensor realized by a photointerrupter having a light-emitting element and a light-receiving element." (a) of FIG. 15 illustrates proper pulse measurement. Each of (b) and (c) of FIG. 15 illustrates improper pulse measurement. (d) of FIG. 15 is a view schematically illustrating a positional relation between a pulse sensor 152 and a fingertip 155 in the proper pulse measurement.

In (a), (b), (c), and (d) of FIG. 15, 150 indicates a mobile device 150. The mobile device 150 is a so-called straight-type mobile phone such as the one illustrated in FIGS. 7 and 8. 151 indicates a display section 151 provided on a front surface (surface with various input keys) of the mobile device 150. 152 indicates that pulse sensor 152 provided on a back surface of the mobile device 150 which is realized by a photointerrupter. 153 indicates a pulse sensor axis 153 for indicating a light emission direction of the photointerrupter. 154 indicates the light emission direction of the photointerrupter.

According to the present invention, the pulse sensor axis 153 of the pulse sensor 152 is defined as an axis which passes through a midpoint between the light-emitting element and the light-receiving element, and which is parallel with the light emission direction 154 of the photointerrupter and is headed in the same direction as the light emission direction 154. 156 indicates a sun 156. FIG. 15 assumes that the pulse meter provided to the mobile device 150 is used outside in the daytime. G indicates a gravitational direction.

As illustrated in (a) of FIG. 15, pulse measurement is performed in such a manner that the attitude of the mobile device 150 is kept so that the pulse sensor 152 provided thereto may face downward (i.e., in the gravitational direction G), and the fingertip 155 receives the weight of the mobile device 150. It follows that substantially the total weight of the mobile device 150 acts on the fingertip 155. As described above, an accurate measured result can be obtained in a case where a weight acting on the fingertip 155 falls within the range from 50 gf to 200 gf. In this case, the pulse sensor axis 153 positionally matches the gravitational direction G, and a positional relation between the pulse sensor axis 153 and the fingertip 155 is as illustrate in (d) of FIG. 15. In this case, further, light from the sun 156 travels downward from a front surface side of the mobile device 150. The light from the sun 156 does not enter, as a direct ray, the pulse sensor 152 realized by the photointerrupter because the light is blocked by the mobile device 150. This makes it possible to reduce a measurement error due to external light.

In (b) of FIG. 15, pulse measurement is performed in such a manner that the pulse sensor 152 faces upward (i.e., toward the sun 156), in contradiction to (a) of FIG. 15. It follows that in the pulse measurement, the fingertip 155 is pressed against the pulse sensor 152. As described above, if a user presses his fingertip 155 against the pulse sensor 152 on his own will, a force acting on the pulse sensor 152 is not always stable. As a result, a measured result thus obtained lacks reliability. In addition, there is a risk in that the direct ray from the sun 156 directly enters the pulse sensor 152. This also leads to a low reliability of a measured result.

In (c) of FIG. 15, the mobile device 150 is supported so that the back surface thereof may be laid down to face the gravitational direction G. Also in this case, a measured result lacks reliability, as is the case with (b) of FIG. 15. That is, a force acting on the pulse sensor 152 is unstable because the force is determined on a user's own will. In addition, there is risk in that the light from the sun 156 directly enters the pulse sensor 152. The way of measurement illustrated in (c) of FIG. 15 is not preferable also from this point of view.

As is evident from the above, in order to obtain an accurate pulse measurement result, it is necessary to hold the mobile device 150 in pulse measurement so that a direction in which the pulse sensor 152 faces and the fingertip 155 may form a proper positional relation, i.e., the pulse sensor axis 153 of the pulse sensor 152 may head in the gravitational direction G.

Therefore, according to the seventh embodiment, the attitude of the mobile device 150 is detected in order that a positional relation between the mobile device 150 and the pulse sensor 152 may be found out in order to check whether or not the attitude allows accurate pulse measurement. If the attitude of the mobile device 150 is not properly taken in the pulse measurement, a user is notified accordingly. Alternatively, if the attitude is properly taken in the pulse measurement, the user is notified accordingly.

(a) and (b) of FIG. 14 are views illustrating how the three-dimensional acceleration sensor detects the attitude of the mobile device 150. First, the following describes an output characteristic of the three-dimensional acceleration sensor, with reference to (a) and (b) of FIG. 14. (a) of FIG. 14 schematically illustrates a three-dimensional acceleration sensor 140 for detecting accelerations acting in the following three axes: the X-axis, the Y-axis, and the Z-axis. (b) of FIG. 14 is a graph showing, for the three axes, outputs of the three-dimensional acceleration sensor 140.

Assume that in (a) of FIG. 14, the three-dimensional acceleration sensor 140 is provided in the mobile device 150 in such a manner that the Z-axis direction is matched with the gravitational direction. In this case, as shown in (b) of FIG. 14, the outputs of the X-axis direction and the Y-axis direction are constant at approximately zero. On the other hand, the output of the Z-axis direction is constant at "1G" (i.e., equal to the gravitational acceleration). In (b) of FIG. 14, the horizontal axis represents time. By finding acceleration components of the three axis directions, it is possible to find the attitude of the three-dimensional acceleration sensor with respect to the gravitational direction. Therefore, a position where the three-dimensional acceleration sensor 140 is provided in the mobile device 150 is determined in advance so that the attitude of the mobile device 150 may be found. (b) of FIG. 14 shows a small output along the Y-axis direction although an output along the Y-axis should be theoretically zero. This is considered to be a measurement error of some kind. At any rate, such an error brings about no obstacle in determination of the attitude.

As illustrated in (d) of FIG. 15, the light emission direction of the photointerrupter of the pulse sensor 152 preferably matches the gravitational direction G in pulse measurement. Therefore, for example, the three-dimensional acceleration sensor 140 is provided to the mobile device 150 so that the Z-axis direction of the three-dimensional acceleration sensor 140 matches the direction of the pulse sensor axis 153. In pulse measurement, accordingly, detected is whether or not the Z-axis direction of the three-dimensional acceleration sensor 140 matches the gravitational direction G. This makes it possible to detect whether or not the mobile device 150 is supported in the proper attitude.

As described above, the pulse sensor axis 153 is preferably headed in the gravitational direction G properly for accurate pulse measurement. However, accurate pulse measurement is still possible even if there is some directional mismatch, provided that the mismatch falls within a predetermined range.

(a) and (b) of FIG. 16 are views illustrating such a case. (a) of FIG. 16 illustrates that mobile device 150 tilted by a degree of θ with respect to the gravitational direction G. (b) of FIG. 16 shows outputs of the pulse meter which were obtained from the following measurement experiments in which the mobile device 150 was tilted.

The measurement experiments were conducted as below by using real mobile devices.

(1) A mobile phone (test model having a weight of 119 g) having a pulse meter was tilted in steps of 15° so that pulse measurement was performed 10 times per angle.

(2) Since a pulse rate inconstantly varies, the following two devices were simultaneously used as comparative devices.

Comparative device 1: A mobile phone having a pulse meter was used in a state of θ=0°.

Comparative device 2: Used was a pulse oximeter (medical apparatus for measuring an oxygen saturation and a pulse rate so as to pinch a fingertip or an earlobe; PULSOX-300i manufactured by Konica Minolta Sensing, Inc.).

In (b) of FIG. 16, the line segment (1) indicates a difference in pulse rate between the tilted mobile phone and the comparative device 1, and the line segment (2) indicates a difference in pulse rate between the tilted mobile phone and the comparative device 2. The line segment (3) indicates a difference between the comparative devices 1 and 2.

Pulse measurement using the comparative devices 1 and 2 was performed every time pulse measurement was performed by using the "mobile phone having a pulse meter" tilted by a "specific angle." However, as described above, the comparative devices 1 and 2 were not tilted by the "specific angle." In (b) of FIG. 16, accordingly, "TILT (DEGREE)" on the X-axis means an "angle in pulse measurement" in which pulse measurement the "mobile phone having a pulse meter" was tilted in steps of 15°. Therefore, "TILT (DEGREE)" does not mean that the comparative devices 1 and 2 were actually tilted in such a way in finding the line segment (3). As is evident from the line segment (3), the outputs of the comparative devices 1 and 2 were stable in the measurement period. The line segments (1), (2), and (3) each represent, as a difference, a total of 10 measurement results.

A measurement error of up to 10 pulses was caused between the comparative devices 1 and 2. This is considered to be due to a difference between measurement methods and a difference between output timings. Therefore, such an error is inevitable. However, in the case of the tilted mobile phone, the pulse measurement evidently became unstable around 60° and greater. For stable pulse measurement, a tilt angle of the mobile phone falls within a range from 0° to 45°, in consideration of some measurement error. Although the range actually varies depending on a weight of the mobile phone, it is considered that the range is determined mainly by whether or not the mobile phone can be stably supported. Even if the mobile phone is a heavy mobile phone which can mathematically apply a force of not less than 50 gf to a fingertip even when tilted by 60°, it is preferable that the tilt angle be up to about 45°, from a viewpoint of reliability of measurement results.

In a case where the mobile phone has a light total weight, and accordingly, a force acting on a fingertip is not more than 50 gf when the mobile phone is tilted, stable pulse measurement cannot be realized, even if the tilt angle is not greater than 45°. A total weight of the mobile phone is an amount which can be found in designing the mobile phone. In addition, it is possible to calculate, in advance, a tilt angle at which the force acting on the fingertip decreases to 50 gf or less, in relation to a position of the pulse sensor 152. Therefore, in the case of a mobile phone which applies a force of not more than 50 gf to a fingertip when the mobile phone is tilted by up to 45°, it is preferable that the mobile phone memorize an allowable range of tilt angles in advance.

FIG. 13 is a block diagram illustrating a main part of the mobile terminal of the seventh embodiment realized on the basis of the knowledge described with reference to FIGS. 14, 15, and 16. FIG. 13 is about a mobile terminal having a pulse meter which can notify a user of whether or not an accurate measurement result can be obtained in pulse measurement.

In FIG. 13, 130 indicates a control section 130 related to a pulse measurement section of the mobile terminal. The control section 130 includes a data obtaining section 134, a pulse measurement control/calculating section 135, and a pulse sensor direction determining section 136. 131 indicates a pulse sensor section 131 constituted by photointerrupter etc. 132 indicates a three-dimensional acceleration sensor 132. The three-dimensional acceleration sensor section 132 can be realized by a conventional sensor.

133 indicates a pulse sensor axis storing section 133 for storing information indicating toward which one of the three axes of the three-dimensional acceleration sensor section 132 the pulse sensor section 131 is directed. As described with reference to FIG. 14, the three-dimensional acceleration sensor 140 can detect accelerations acting in the three axis directions of: the X-axis direction (horizontal direction in FIG. 14); the Y-axis direction (front-back direction in FIG. 14); and the Z-axis direction (vertical direction in FIG. 14). In addition, the three-dimensional acceleration sensor 140 can find an acceleration acting in any direction, from the accelerations of the three axis directions.

For example, assume that the pulse sensor axis 153 and the three-dimensional acceleration sensor 140 are provided in the mobile device 150 so that the direction of the pulse sensor axis 153 may match the Z-axis direction of the three-dimensional acceleration sensor 140. In this case, the pulse sensor axis storing section 133 stores information indicative of "Z axis." In this case, the information and the direction of the pulse sensor axis 153 match each other. Therefore, the information indicative of "Z-axis" is taken as a direction of the pulse sensor axis 153 so as to be used in comparison with the gravitational direction G.

137 indicates a display/notification section 137 for displaying a pulse measurement result and notifying a user of whether or not the mobile device is supported in a proper attitude in pulse measurement. Assume that a large liquid crystal screen can be adopted as the display/notification section 137. In this case, the display/notification section 137 can display an image showing a proper attitude in which the mobile terminal is supported, in such cases where a user holds the mobile terminal so that the mobile terminal may take an improper attitude, or a user pushed down a button for pulse measurement. Thus, the user can easily learn the proper attitude.

In pulse measurement, a user pushes down the button or the like (not illustrated) to instruct that pulse measurement be started, and puts his fingertip on the pulse sensor section 131. Needless to say, it is possible to instruct that pulse measurement be started, while putting a fingertip on the pulse sensor section 131. The data obtaining section 134 obtains data from the pulse sensor section 131 so as to supply the data to the pulse measurement control/calculating section 135. A pulse rate is calculated therein. The pulse rate is supplied to the display/notification section 137.

On the other hand, the three-dimensional acceleration sensor section 132 supplies, to the pulse sensor direction determining section 136, attitude information obtained by the three-dimensional acceleration sensor section 132, i.e., attitude information of the mobile terminal 150. The pulse sensor direction determining section 136 determines whether or not the pulse sensor section 131 is directed in a proper direction, on the basis of: the information from the pulse sensor axis storing section 133 which information is stored therein in advance; and the information from the three-dimensional acceleration sensor section 132. The determination result is supplied to the display/notification section 137. It can be varied in many ways when and how a user is notified in actual pulse measurement of whether or not the pulse sensor section 131 is directed in the proper direction. Details thereof are described later with reference to FIGS. 17 to 23.

FIG. 17 illustrates states of use of a pulse meter of a slidable mobile phone 170. FIG. 18 illustrates states of use of a pulse meter of a foldable mobile phone 180 in the unfolded state. FIG. 19 illustrates states of use of the pulse meter of the foldable mobile phone 180 in the folded state. In FIGS. 17, 18, and 19, members with the same reference signs as those in FIGS. 15 and 16 are the same as those in FIGS. 15 and 16. Therefore, the following omits the details thereof.

In pulse measurement using the slidable mobile phone 170, as illustrated in (a) and (b) of FIG. 17, a user holds the slidable mobile phone 170 so that a display section 171 thereof may face upward, and puts the fingertip 155 on a pulse sensor 152 from below which is provided on an opposite surface to the display section 171. In this case, as is evident from (b) of FIG. 17, the gravitational direction G and the direction of the pulse sensor axis 153 match each other. In this case, the display section 171 displays a message that the slidable mobile phone 170 is in the proper attitude in pulse measurement. In FIG. 17, the display section 171 displays "OK."

In (c) and (d) of FIG. 17, the slidable mobile phone 170 is not in the proper attitude in pulse measurement. Therefore, a warning lamp 172 (red lamp or the like) provided on the opposite surface to the display section 171, e.g., blinks so as to notify a user that the user does not properly use the pulse sensor 152. Alternatively, a warning sound can be generated. In this case, as is evident from (d) of FIG. 17, the gravitational direction G is opposite to the direction of the pulse sensor axis 153.

In (a) and (b) of FIG. 18, the foldable mobile phone 180 is in the proper attitude in pulse measurement. Accordingly, a display section 181 notifies a use of this. In (a) of FIG. 18, the display section 181 displays "OK." Also in this case, as is evident from (b) of FIG. 18, the gravitational direction G matches the direction of the pulse sensor axis 153.

In (c) and (d) of FIG. 18, the foldable mobile phone 180 is not in the proper attitude in pulse measurement. Accordingly, a second display section 182 or the like notifies this. In (c) of FIG. 18, the second display section 182 displays "NG." In this case, as is evident from (d) of FIG. 18, the gravitational direction G is opposite to the direction of the pulse sensor axis 153.

FIG. 19 illustrates states of use of the foldable mobile phone 180 in the folded state. In (a) and (b) of FIG. 19, the foldable mobile phone 180 in the folded state is in the proper attitude in pulse measurement. Accordingly, the second display section 182 notifies a user of this. In (a) of FIG. 19, the second display section 182 displays "OK." In this case, as is evident from (b) of FIG. 19, the gravitational direction G matches the direction of the pulse sensor axis 153.

In (c) and (d) of FIG. 19, the foldable mobile phone 180 is not in the proper attitude in pulse measurement. Accordingly, for example, a warning lamp 183 etc. notify a user of this. The warning lamp 183 is provided on a surface on which the second display section 182 is provided. In this case, as is evident from (d) of FIG. 19, the gravitational direction G is opposite to the direction of the pulse sensor axis 153.

With reference to FIGS. 20 to 23, the following describes a pulse measurement flow containing a timing when to notify a user of whether or not the pulse sensor is directed in the proper direction. The following assumes that the pulse sensor is directed in the proper direction (i.e., the pulse sensor axis 153 matches the gravitational direction) in a case where the Z-axis of the three-dimensional acceleration sensor matches the gravitational direction.

The following describes a first pulse measurement flow, with reference to FIG. 20. If a pulse measurement button is pushed down in step 1 (hereinafter, referred to as S1), the three-dimensional acceleration sensor is turned on (S2). Then, an acceleration sensor value (i.e., orientation of the three-dimensional acceleration sensor) is obtained (S3). Then, it is determined whether or not the Z-axis direction of the three-dimensional acceleration sensor matches the gravitational direction (S4). If YES in S4, a pulse rate is measured (S5), and the measured result is displayed on the display section. If NO in S4, a warning is accordingly given to a user (S6). In this case, a pulse rate is not measured.

The following describes a second pulse measurement flow, with reference to FIG. 21. If the pulse measurement button is pushed down (S1), pulse measurement is started first (S2). Then, an acceleration sensor value (i.e., orientation of the three-dimensional acceleration sensor) is obtained (S3). Then, it is determined whether or not the Z-axis direction of the three-dimensional acceleration sensor matches the gravitational direction (S4). If YES in S4, pulse measurement is carried out, and the measurement result is displayed on the display section (S5). If NO in S4, the pulse measurement is halted (S6).

The following describes a third pulse measurement flow, with reference to FIG. 22. If the pulse measurement button is pushed down (S1), pulse measurement is started first (S2). Then, an acceleration sensor value (i.e., orientation of the three-dimensional acceleration sensor) is obtained (S3). Then, it is determined whether or not the Z-axis direction of the three-dimensional acceleration sensor matches the gravitational direction (S4). If YES in S4, pulse measurement is carried out, and the measurement result is displayed on the display section (S5). If NO in S4, a warning is accordingly given to a user (S6). Then, pulse measurement information is deleted (S7).

The following describes a forth pulse measurement flow, with reference to FIG. 23. If the pulse measurement button is pushed down (S1), pulse measurement is started first (S2). Then, an acceleration sensor value (i.e., orientation of the three-dimensional acceleration sensor) is obtained (S3). Then, it is determined whether or not the Z-axis direction of the three-dimensional acceleration sensor matches the gravitational direction (S4). If YES in S4, pulse measurement is carried out, and the measurement result is displayed on the display section (S5). If NO in S4, a flag indicative of improper measurement is set (S6). Then, a message indicating improper measurement and a pulse rate are displayed on the display section (S5).

The above states "it is determined whether or not the Z-axis direction of the three-dimensional acceleration sensor matches the gravitational direction." However, as described with reference to FIG. 16, even if the directions does not accurately match, still, accurate pulse measurement is possible, provided that a tilt angle falls within a certain range (from 0° to 45°). Therefore, "whether or not . . . matches . . . " can be taken as "whether or not a tilt angle falls within the allowable range."

Further, as described above, stable pulse measurement requires a force of not less than 50 gf acting on a fingertip. Therefore, in a case where a mobile phone has a light total weight, and accordingly, a force of not more than 50 gf acts on the pulse sensor when the mobile phone is tilted by an angle from 0° to 45°, the "allowable range" can be taken as an "angular range within which a force acting on the pulse sensor is not less than 50 gf when the mobile phone is tilted."

From a total weight of the mobile phone and a position where the pulse sensor is provided, it is possible to calculate, in advance, a tilt angle at which the force acting on the pulse sensor decreases to 50 gf or less. In this case, an "allowable angular range storing section" for storing such an "allowable angular range found in advance by calculation" is provided in the pulse sensor direction determining section 136 in FIG. 13. The allowable angular range is taken into consideration in determining whether or not the pulse sensor is directed in the proper direction.

The embodiments above deal with, as one example, a mobile terminal having a communication function, i.e., a mobile phone. However, the present invention is applicable not only to mobile phones but also to mobile terminals, such as PDAs, having no communication function. In addition, a mobile terminal of the present invention can be that mobile terminal having a pulse meter which selectively has required functions. Such a mobile terminal does not necessarily have all the functions.

The embodiments above mainly describe a position of the sensor along a lengthwise direction (longer direction) of the casing of the mobile phone. As for a widthwise direction (shorter direction), it is preferable to provide the sensor substantially in the barycentric position along the widthwise direction. This makes it possible to reduce swinging of the mobile phone which is caused in the shorter direction when the sensor is supported by a fingertip. In the way of holding illustrated in (b) of FIG. 3, which way seems to be particularly common, a hand does not support areas extending, along the shorter direction, from the sensor to both sides. Therefore, it is effective, for stable pulse measurement, to provide the sensor in the barycentric position along the shorter direction. Usually, the barycentric position lies around a midpoint along the shorter direction.

The lengthwise direction and the widthwise direction in the previous paragraph can be defined such that the lengthwise direction is a top-to-bottom direction of a character and a graph (particularly, a character and a graph for showing a measurement result), and the widthwise direction is a right-to-left direction thereof. The mobile phones in the embodiments above allow a user to use a finger cushion in pulse measurement by stretching the finger to some extent when putting the fingertip on the sensor. A finger cushion is a part on which an excessive force is unlikely to act, and which less shakes. This leads to stable pulse measurement. In a case where the mobile phone supported in such a state displays a character, a picture, and a graph so that an upper direction thereof may be a direction that the fingertip points, viewability thereof is increased.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

As described above, a mobile terminal of an invention of the present application includes: a main body housing an electronic device; a display section or an operation section, being provided on a first surface of the main body; and a sensor for detecting a pulse, the sensor being provided to a first end portion of a second surface of the main body, the sensor being constituted by a light-emitting element and a light-receiving element, and the sensor being provided so that a force acting on the sensor may fall within a range from 50 gf to 200 gf in a case where the mobile terminal is supported from below at a position of the sensor and at a position in a second end portion of the second surface.

Further, a mobile terminal of another invention of the present application includes: a main body housing an electronic device; and a sensor for detecting a pulse, the main body being constituted by a first casing having a display section on its first surface, a second casing having an operation section on its first surface, and a joint for foldably joining the first casing and the second casing so that the first surface of the first casing and the first surface of the second casing may face each other, the sensor being provided to a first end portion of a second surface of the second casing, the first end portion being closer to the joint than a second end portion of the second casing, and the sensor being provided so that a force acting on the sensor falls within a range from 50 gf to 200 gf in a case where the mobile terminal is supported from below at a position of the sensor and at a position in the second end portion of the second surface of the second casing.

A mobile terminal of further another invention of the present application further includes: a three-dimensional acceleration sensor; a pulse sensor axis storing section; and a pulse sensor direction determining section, on the basis of (i) information indicative of an attitude of the mobile terminal which attitude is detected by the three-dimensional acceleration sensor and (ii) pulse sensor axis information supplied from the pulse sensor axis storing section, the mobile terminal determining, in pulse measurement, whether or not the sensor is directed in the gravitational direction, in order to notify a user of whether or not the mobile terminal is in a proper attitude.

This makes it possible to provide various types of mobile terminals which cause no difficulty in always carrying with a user, and which have a pulse meter by which anyone can measure a pulse rate easily and accurately in a short time.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The present invention provides that mobile terminal having a pulse meter which can be always carried with a user and which realizes easy stable pulse measurement. Such a mobile terminal has a high usability since it is highly important to know one's own pulse rate during exercise from a viewpoint of appropriate exercise.

REFERENCE SIGNS LIST

1 First casing
2 Second casing
3 Joint
4 First display section
5 Second display section
6 Input keys
7 Operation keys
8 Microphone
9 Speaker
11 Camera
12 Operation keys
15 Sensor realized by reflective photointerrupter
24 Fingertip 40 Reflective photointerrupter (sensor)
42 Light-emitting element
43 Light-receiving element
150 Mobile device
151 Display section
152 Pulse sensor
153 Pulse sensor axis
155 Fingertip
156 Sun
170 Slidable mobile phone
171 Display section of slidable mobile phone
172 Warning lamp
180 Foldable mobile phone
181 Display section of foldable mobile phone
182 Second display section
183 Warning lamp

The invention claimed is:

1. A mobile terminal comprising:
a main body housing an electronic device;
a display section or an operation section, being provided on a first surface of the main body;
a sensor for detecting a pulse, the sensor being provided on a second surface of the main body, the sensor having a light-receiving element,
the mobile terminal having a weight of not more than 200 gf in order to facilitate the pulse detection by the sensor, and
an attitude detector sensor configured to detect an attitude of the mobile terminal; and
a control section configured to (i) perform determination as to whether or not a direction of the sensor matches a gravitational direction, and (ii) control, in accordance with the determination, (I) notification of information or (II) pulse detection, the control section performing the determination on the basis of the attitude of the mobile terminal, the attitude being detected by the attitude detector sensor.

2. The mobile terminal as set forth in claim 1, having a weight of not less than 50 gf, in order to facilitate the pulse detection by the sensor.

3. The mobile terminal as set forth in claim 1, further comprising a second display section on the second surface of the main body,
in a case where the control section determines that the direction of the sensor does not match the gravitational direction, the control section notifying, via the second display section, a user that the sensor is not properly used.

4. The mobile terminal as set forth in claim 1, comprising a pulse sensor axis storing section, the pulse sensor axis storing section storing information indicative of a direction, with respect to the main body, of an axis of the sensor,
the attitude detector sensor being a three-dimensional acceleration sensor,
in order to notify a user of whether or not the mobile terminal is in a proper attitude, the control section determining, when the sensor detects a pulse, whether or not the axis of the sensor is directed in the gravitational direction, on the basis of (a) information indicative of the attitude of the main body of the mobile terminal, the attitude being detected by the attitude detector sensor, and (b) pulse sensor axis information supplied by the pulse sensor axis storing section.

5. The mobile terminal as set forth in claim 4, wherein the control section determines that the mobile terminal is in the proper attitude in a case where a direction of the axis of the sensor falls within a range from 0° to 45° with respect to the gravitational direction, and a force acting on the sensor is not less than 50 gf when the mobile terminal is tilted.

6. The mobile terminal as set forth in claim 1, wherein the sensor is provided in a barycentric position of the mobile terminal, which barycentric position the mobile terminal has on the second surface.

7. The mobile terminal as set forth in claim 1, wherein:
the main body includes a plurality of casings including the first casing and the second casing;
adjustment of a position of the first casing with respect to a position of the second casing brings the sensor to or near a barycentric position of the mobile terminal, which barycentric position the mobile terminal has on the second surface.

8. The mobile terminal as set forth in claim 1, wherein the sensor has a light-emitting element.

9. The mobile terminal as set forth in claim 1, wherein the sensor is provided to an end portion of the second surface of the main body.

10. A mobile terminal comprising:
a main body housing an electronic device;
a display section or an operation section, being provided on a first surface of the main body;
a sensor for detecting a pulse, the sensor being provided on a second surface of the main body, the sensor having a light-receiving element,
the mobile terminal having a weight of not more than 200 gf in order to facilitate the pulse detection by the sensor,
detecting an attitude of the mobile terminal with an attitude detector sensor; and
performing determination as to whether or not a direction of the sensor matches a gravitational direction, and controlling, in accordance with the determination, (I) notification of information or (II) pulse detection, the determining step performing the determination on the basis of the attitude of the mobile terminal, the attitude being detected by the attitude detector sensor.

11. A mobile terminal, comprising:
a main body housing an electronic device, the main body having a first main surface, a second main surface and side surfaces connecting the first and second main surfaces;
a display section or an operation section, being provided on a first main surface of the main body;
a pulse sensor being provided on a second main surface of the main body at a sensor position, wherein the sensor position is located such that when the mobile terminal is bottom-supported near an end portion of the second main surface and at the sensor position, the mobile terminal's weight applies a force to the pulse sensor in a range from 50 gf to 200 gf.

12. The mobile terminal as set forth in claim 11, wherein the sensor position is provided at a barycentric position on the second main surface of the mobile terminal.

* * * * *